United States Patent
Figley et al.

(12) 
(10) Patent No.: US 6,668,828 B1
(45) Date of Patent: Dec. 30, 2003

(54) SYSTEM AND ELEMENTS FOR MANAGING THERAPEUTIC GAS ADMINISTRATION TO A SPONTANEOUSLY BREATHING NON-VENTILATED PATIENT

(75) Inventors: Curtis B. Figley, Edmonton (CA); Darin W. Hunt, Edmonton (CA); Christopher C. Miller, North Vancouver (CA)

(73) Assignee: Pulmonox Technologies Corporations, Edmonton (CA)

( * ) Notice: Subject to any disclaimer, the term of this patent is extended or adjusted under 35 U.S.C. 154(b) by 266 days.

(21) Appl. No.: 09/688,229

(22) Filed: Oct. 16, 2000

(51) Int. Cl.[7] .............................................. A61M 16/00
(52) U.S. Cl. .............................. 128/204.18; 128/204.22
(58) Field of Search .......... 128/204.18, 204.22–204.25, 128/204.29, 205.11, 207.12, 206.11, 206.15, 207.18, 205.24

(56) References Cited

U.S. PATENT DOCUMENTS

| | | | |
|---|---|---|---|
| 3,794,072 A | | 2/1974 | Diedrich |
| 3,906,996 A | | 9/1975 | DePass |
| 3,977,432 A | | 8/1976 | Vidal |
| 4,216,769 A | | 8/1980 | Grimes |
| 4,248,218 A | | 2/1981 | Fischer |
| 4,266,540 A | | 5/1981 | Panzik |
| 4,354,488 A | | 10/1982 | Bartos |
| 4,454,880 A | | 6/1984 | Muto |
| 4,572,177 A | | 2/1986 | Tiep |
| 4,681,099 A | | 7/1987 | Sato |
| 4,685,456 A | * | 8/1987 | Smart .................. 128/205.22 |
| 5,005,571 A | | 4/1991 | Dietz |
| 5,086,767 A | * | 2/1992 | Legal ................... 128/205.18 |
| 5,320,092 A | * | 6/1994 | Ryder .................. 128/202.22 |
| 5,372,129 A | * | 12/1994 | Ryder .................. 128/205.11 |
| 5,803,064 A | * | 9/1998 | Phelps et al. ......... 128/203.12 |
| 5,839,433 A | | 11/1998 | Higgenbottam |
| 5,890,490 A | * | 4/1999 | Aylsworth et al. ..... 128/203.12 |
| 6,024,088 A | * | 2/2000 | Ishikawa et al. ....... 128/204.21 |
| 6,142,149 A | * | 11/2000 | Steen ................... 128/204.23 |
| 6,186,143 B1 | * | 2/2001 | Baum ................... 128/205.11 |
| 6,253,764 B1 | * | 7/2001 | Calluaud ............... 128/204.18 |
| 6,253,766 B1 | * | 7/2001 | Niles et al. ............ 128/204.24 |
| 6,263,873 B1 | * | 7/2001 | Hedenberg ............ 128/204.28 |
| 6,308,703 B1 | * | 10/2001 | Alving et al. ......... 128/203.12 |

OTHER PUBLICATIONS

Journal of Pediatrics, Sep. 1998, pp 453–456.
1995 ATS Abstracts, pp. A85–A87.
American Journal of Respiratory and Critical Care Medicine, v151, 1995, pp. 1263–1266.
Critical Care Medicine, vol 22, No. 6, Jun. 1994, pp. 930–938.
Chest, 109/6/Jun. 1996, pp. 1545–1549.

* cited by examiner

*Primary Examiner*—Weilun Lo
*Assistant Examiner*—Teena Mitchell
(74) *Attorney, Agent, or Firm*—Terry M. Gernstein

(57) ABSTRACT

A system controls and manages administration of a therapeutic gas, such as NO, $O_2$, or the like, to a spontaneously breathing, non-ventilated patient such that concentrated NO is as low as reasonably possible while delivering the desired amount of NO to the distal portions of the lungs. The system includes an entrainment cell that provides remote, turbulent mixing with low temporal latency and can be used with a nasal cannula or a mask. The entrainment cell uses room air to dilute the therapeutic gas; however, supplementary gases can also be used. A baffle can be included to promote mixing and a flow sensor can also be used if desired. Multiple ports can be included in the entrainment cell. An equalizing valve is also disclosed.

41 Claims, 24 Drawing Sheets

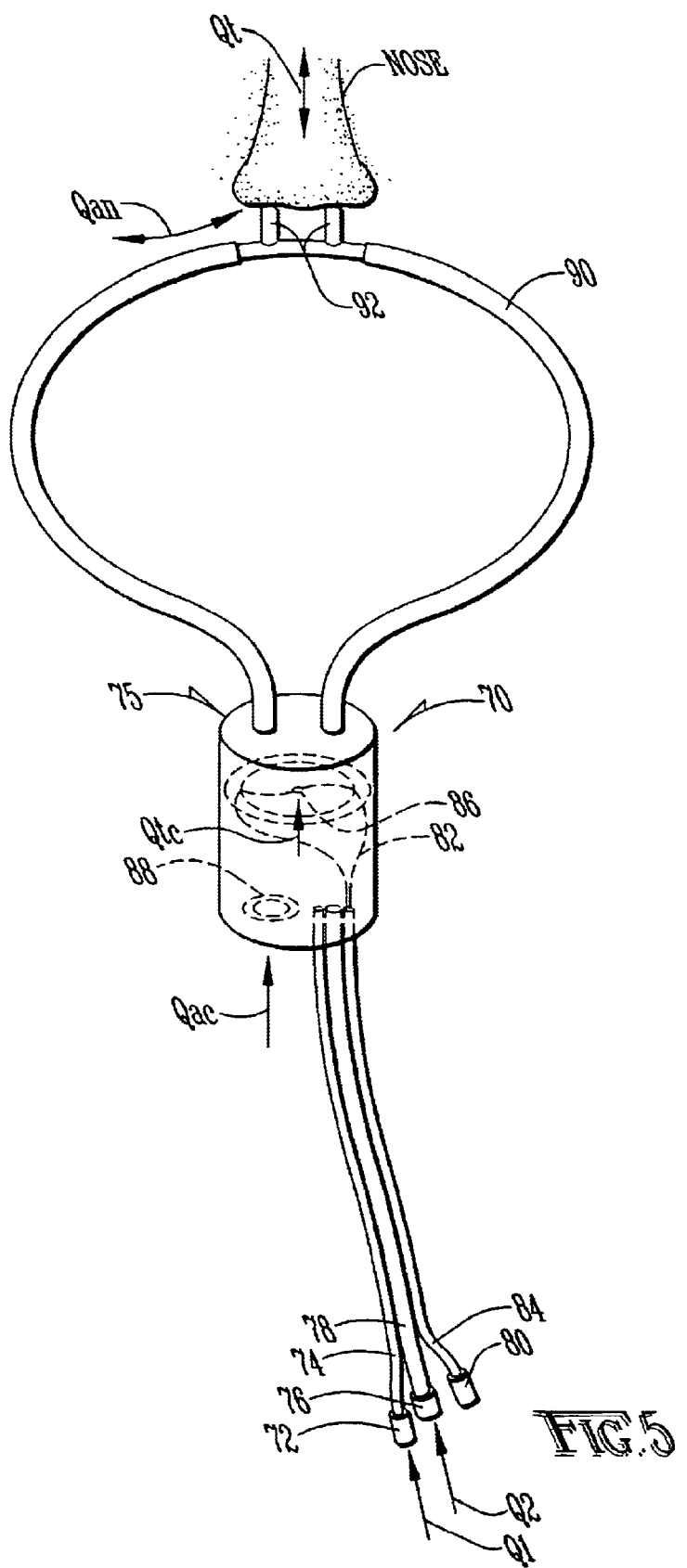

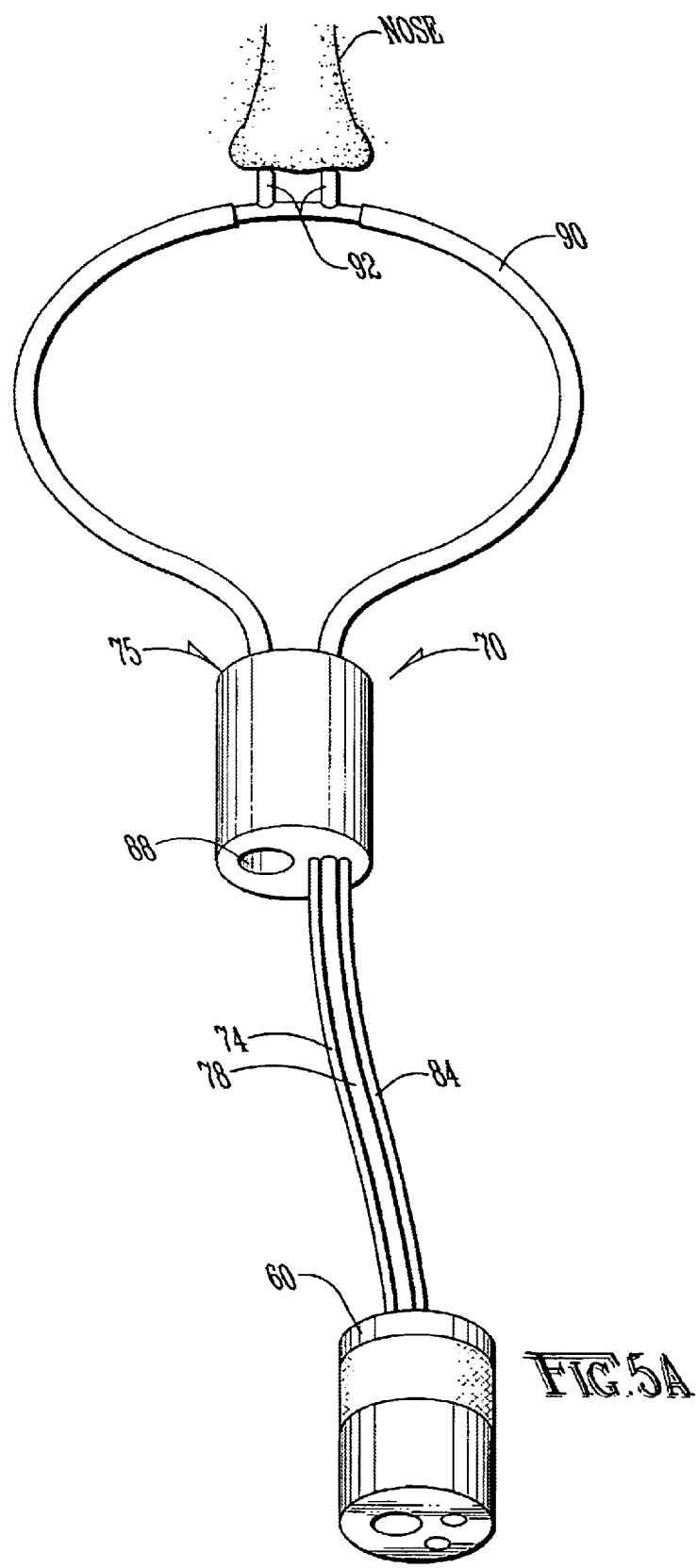

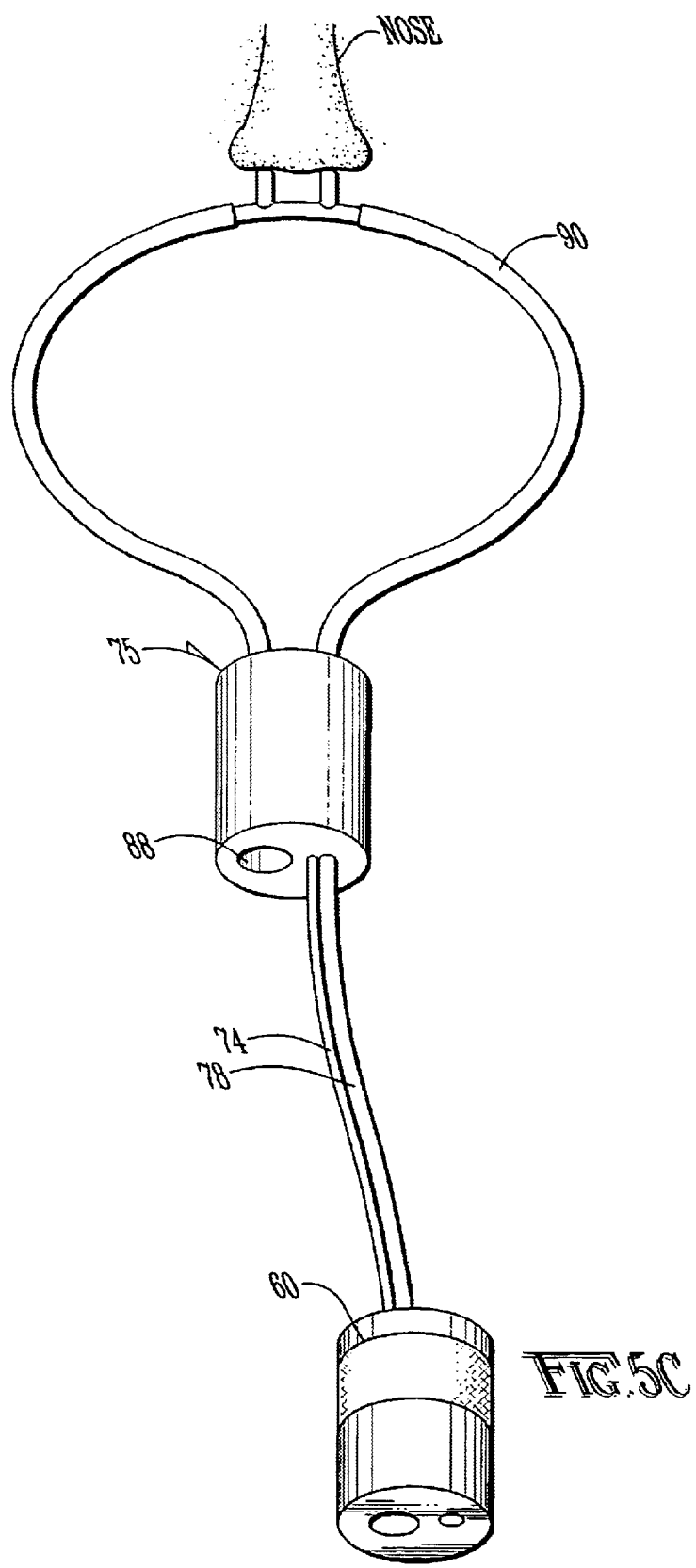

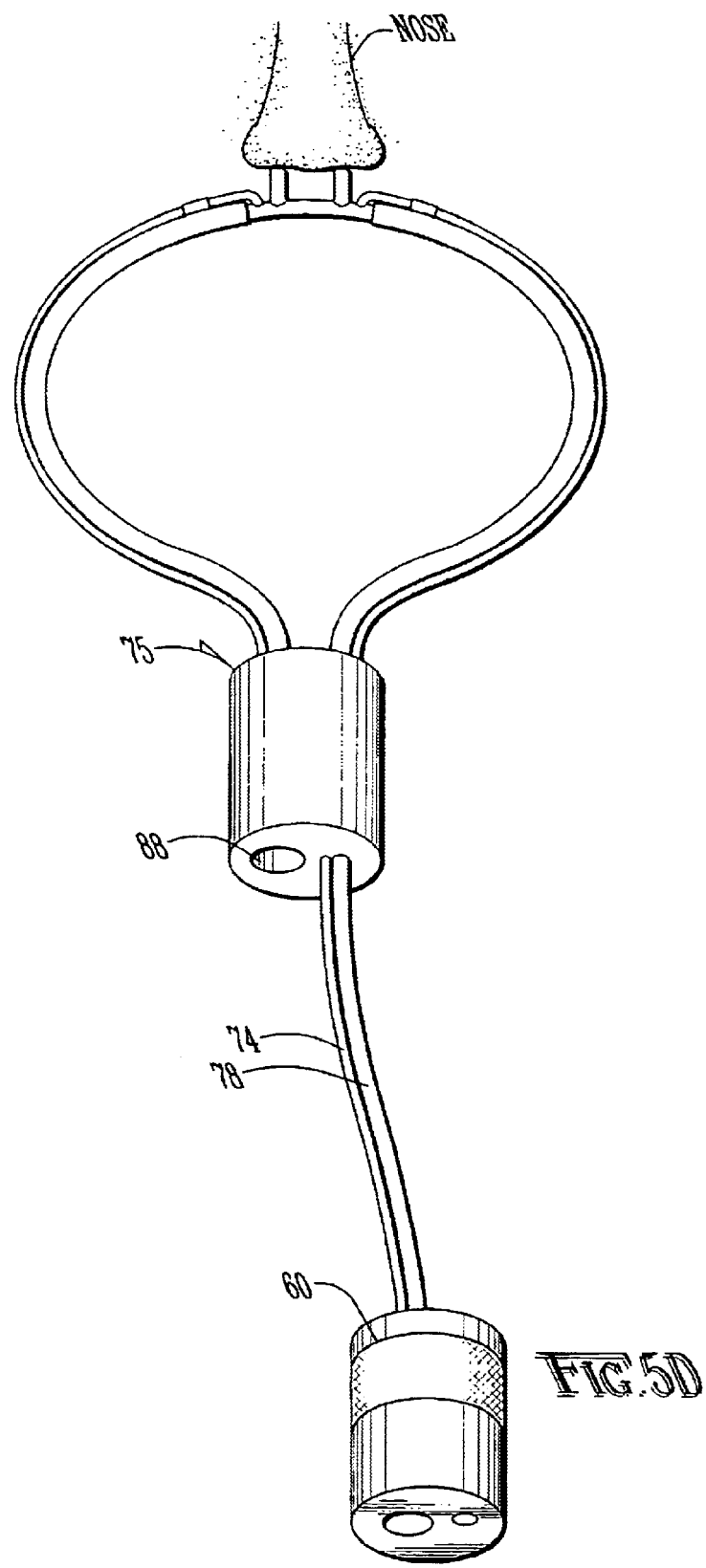

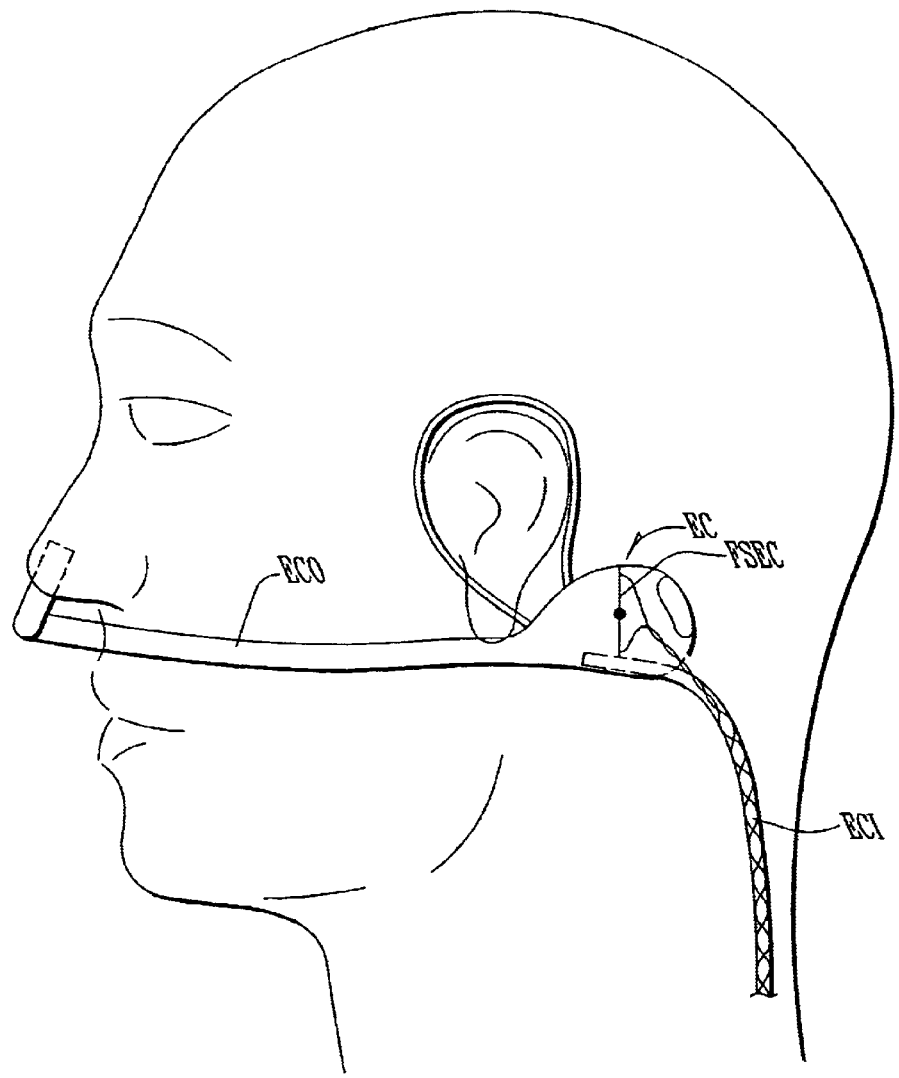

SYSTEM AND ELEMENTS FOR MANAGING THERAPEUTIC GAS ADMINISTRATION TO A SPONTANEOUSLY BREATHING NON-VENTILATED PATIENT

TECHNICAL FIELD OF THE INVENTION

The present invention relates to the general art of surgery, and to the particular field of introducing material to a patient for therapeutic or diagnostic purposes, most specifically, the invention relates to NO therapy.

BACKGROUND OF THE INVENTION

The use of therapeutic gases to treat a human or animal patient has been known in the art for many years. A number of different gases may be added to a respiratory gas that is inhaled by a spontaneously breathing, non-ventilated patient. These gases may be used to achieve some therapeutic effect, service a diagnostic function or have some other desirable purpose. Such gases will be referred to herein as "therapeutic gases." One skilled in the delivery of therapeutic gas will understand that the disclosure can be used to teach either human or animal patients. Accordingly, no limitation to human is intended by references to patient in this disclosure.

One therapeutic gas is nitric oxide (NO), which is administered by inhalation in low concentrations to treat primary or secondary pulmonary hypertension or other diseases. In many cases, nitric oxide or other therapeutic gases come from a high concentration source such as a high concentration compressed gas cylinder. The gas source may be pure or may contain some concentration of therapeutic gas in a carrier gas. There may also be cases where more than one therapeutic gas is used, with or without a carrier gas or gases. It is often necessary to dilute therapeutic gas to a lower concentration and mix it with air and/or oxygen prior to delivery to the patient. This dilution may be necessary to achieve a desired dosage concentration and/or to avoid or reduce adverse bioeffects that may occur if high concentration gas is delivered to the patient. If the therapeutic/carrier gas is not sufficiently oxygenated, it is necessary to mix it with air prior to delivery to the patient. In some cases, it is necessary to add supplemental oxygen to the mixture to avoid a hypoxic respiratory mixture or to enrich the oxygen content of the respiratory gas above twenty-one percent. In the latter case, the oxygen will also be considered as a therapeutic gas.

NO is one of a number of therapeutic gases that are administered to a patient and require dilution from a high concentration form to a lower, safer concentration before administration to a patient. No will be the primary focus of this disclosure; however, one skilled in the surgical arts will understand that the disclosure can be used to teach other gases as well. Accordingly, no limitation to NO is intended by the references to NO in this description.

The art contains several devices and systems to deliver therapeutic gas to a spontaneously breathing, non-ventilated patient. However, as will be discussed, each of the known systems and devices has drawbacks.

A system that has continuous flow to a mask is one such known system. A therapeutic gas, oxygen and air are supplied from sources such as compressed gas cylinders or a hospital wall. A continuous flow of these gases is titrated together before delivery to a patient. The flow rate of each gas is set to achieve the desired concentration of the therapeutic gas and oxygen in the respiratory gas. The total flow rate is set greater than the peak inspiratory flow rate. If a reservoir bag is added to the inspiratory portion of the overall circuit, then the total flow can be reduced, but must still be greater than the minute volume of the patient. The mixed gas is connected into the mask, from which the patient inhales. Exhaled gas and excess inhalation gas flow from an outlet side of the mask and may be scavenged. This system has the disadvantage of wasting gas since not all therapeutic gas is inhaled by the patient. Scavenging is required to prevent the therapeutic gas from entering the environment. In addition, large volumes of air and/or oxygen must be supplied to dilute/mix the therapeutic gas. Also, therapeutic gas is delivered to the entire respiratory tract, not just the areas where it is needed. This may increase adverse bioeffects and the possibility of undesirable reaction products from the therapeutic gas. The mask also makes eating and talking difficult and is also aesthetically unappealing. Still further, a mask may make some patients nervous and cause anxiety by making them feel confined.

Yet another system uses a bolus pulse of therapeutic gas to a mask. In this system, therapeutic gas is delivered to the patient as a bolus of gas that is delivered via the mask. The bolus of therapeutic gas is delivered over a short period of time and is not significantly diluted by inhaled air or supplemental oxygen. Supplemental oxygen may also be delivered via the mask. The patient's breathing waveform is monitored and the bolus of therapeutic gas is delivered to the mask intermittently, in synchronization with the respiratory waveform so that the therapeutic gas is inhaled at a set phase of the respiratory waveform. The bolus is preceded and/or followed into the respiratory tract by air/oxygen. This system and method has the disadvantage that it does not dilute the therapeutic gas, so a high concentration source cannot be used. In addition, the short duration of the bolus means that a higher concentration of therapeutic gas is required to deliver the same number of molecules of the gas to the patient. This could have adverse bioeffects. This method does not have the flexibility of varying the concentration of the therapeutic gas at various times during inspiration. The mask has the same drawbacks as heretofore discussed.

Yet another system and method uses an undiluted pulse via a nasal cannula. A nasal cannula is a device that can be used to transmit therapeutic gas from one or more therapeutic gas sources to the nose of a patient for inhalation. It includes one or more connectors at one end of the device to connect to one or more therapeutic gas sources, one or more long lumens to transmit the gas, and nasal prongs at the other end to inject one or more therapeutic gases into the patient's nose. The word "lumen" will be used in this disclosure to represent a long, narrow, flexible fluid conduit that is less than 0.8 cm in internal diameter. A nasal cannula is typically much less obtrusive than a mask and allows the patient to talk and eat while receiving gas therapy. In the method of undiluted pulse delivery via a nasal cannula, therapeutic gas is delivered via a nasal cannula as an intermittent flow pulse during inspiration. Air pressure in the nares drops at the start of inspiration. This pressure drop is transmitted through the cannula and is detected in the pulse delivery device. Therapeutic gas flow is turned on for a period of time during inspiration. The therapeutic gas flows directly into the nares from the cannula. While overcoming many disadvantages associated with a mask, this method also has disadvantages as practiced in the known art. For example, the therapeutic gas is not diluted prior to entering the nares in many known systems. If a high concentration source is used, high concentration gas may contact the tissues before it is diluted in the respiratory tract. This may have adverse bioeffects. If lower concentration gas is used, the source lifetime/size advantages of a high concentration source are lost. Also, the final dilution concentration in the respiratory tract is limited. It is lower for any given volume of therapeutic/carrier gas, and this volume must be limited to avoid a hypoxic respiratory gas mixture. Still further disadvantages will be discussed below in reference to the use of known cannulas.

Still another known method and system for administering therapeutic gas to a patient includes an undiluted pulse via a nasal cannula and oxygen via another lumen. In this method, gas may be delivered as discussed above, with the addition of supplemental oxygen delivered via a second lumen in a dual lumen cannula. This method has all the disadvantages discussed above, except that it allows a higher diluted concentration to be delivered to the respiratory tract without having a hypoxic mixture. This has the accompanying disadvantage of requiring a supplemental oxygen source.

A diluted pulse to a cannula can also be used. In this method, the therapeutic gas may be delivered by a nasal cannula and diluted prior to entering the nares. This can be done by mixing it with a diluent gas from a diluent gas source before it leaves the cannula. The therapeutic gas concentration can be reduced to a safe level prior to entering the nares. It is further diluted in the respiratory tract by entrained air from the room. This method has the disadvantage of requiring a diluent gas source. If supplemental oxygen therapy is desired, oxygen or enriched air may be used as the diluent gas, but it is more difficult to control the oxygen concentration reaching the respiratory tract because a minimum diluent gas flow is required to dilute the therapeutic gas to a safe concentration in the cannula.

Still another known method includes a continuous flow of therapeutic gas and supplemental oxygen delivered to the patient via a nasal cannula. This method has therapeutic gas delivered continuously via a nasal cannula by titrating the therapeutic gas with air and/or oxygen before the cannula or in the cannula before it reaches the nares. The therapeutic gas concentration can be reduced to a safe level prior to entering the nares. It is further diluted in the respiratory tract by entrained air from the room, This method has the disadvantage of requiring a diluent gas source. If supplemental oxygen is required, a source of air and a source of oxygen will be required or it will be difficult to control the oxygen concentration reaching the respiratory tract.

Yet another known method of administering therapeutic gas to a patient includes use of a transtracheal catheter. In this method, therapeutic gas can be delivered directly to the trachea of the patient via a transtracheal catheter. Therapeutic gas flow might be continuous or pulsed. This method has the disadvantage that the therapeutic gas is not diluted prior to entering the respiratory tract. If a high concentration source is used, high concentration gas may contact the tissues before it is diluted in the respiratory tract. This may have adverse bioeffects. If lower concentration gas is used, the source lifetime/size advantages of a high concentration source are lost. Also, the final diluted concentration in the respiratory tract is limited. It is lower for any given volume of therapeutic/carrier gas and this volume must be limited to avoid a hypoxic respiratory gas mixture. The transtracheal catheter is invasive, which is often undesirable.

The art has also developed methods which deliver therapeutic gas to a patient during certain times. In such systems, gas delivery is pulsed on during inspiration. Other systems also include means for adjusting dosages, durations, flow rates and the like.

It is noted that not every patient has the same breathing pattern as other patients so a pulse configuration and time that is suitable for one patient may not be completely efficient for another patient. The shape of the gas pulse (flow rate versus time profile) of a first gas may be an approximately arbitrary shape. Some devices for pulsed gas delivery to spontaneously breathing patients use a pulse of a set flow rate and vary the duration of the pulse to change the dosage of gas to a patient. This results in an approximately rectangular flow versus time shape of the pulse. Other devices use a constant pulse duration but flow rate is altered to change dosage. Flow rate is constant during any single pulse and the pulse shape is approximately rectangular.

There is a need for a system that is adaptable to customizing the pulse shape, can easily adjust the dose, is adaptable to various conditions and modes of operation for various patients having individual requirements and is easily maintained by various caregivers.

Still further, some patients require delivery of more than one therapeutic gas. Therefore, there is a need for a system that is amenable to delivering more than one therapeutic gas to a patient if necessary.

Since many patients have individual requirements, it is necessary that a therapeutic gas delivery system be amenable to use by a variety of caregivers ranging in expertise from professional nurses and doctors to laymen in a home environment. In order to be most efficient and effective, the system should efficiently deliver therapeutic gas to the patient at all desired times, even if a primary source of gas is being changed. This may be particularly important in some applications such as nitric oxide therapy where interruption of the therapy can result in a "rebound" effect where patient symptoms become as bad as or worse than they were before the therapy began. To be most versatile, the system should be amenable to use with either a nasal cannula (nasal prongs) or a mask and be easily used, monitored and maintained by a variety of caregivers.

There is thus a need for a system which is amenable to use by a variety of caregivers and which has means for delivering therapeutic gas in an uninterrupted manner when desired.

More specifically, even though there are several cannulas known in the art, these known cannulas have various drawbacks that may vitiate advantages obtained from customizing a therapeutic gas delivery system in order to overcome the drawbacks associated with known systems.

For example, known cannulas do not have means for efficiently controlling mixing of gases and do not have a gas mixing area that is most efficient or most efficiently located.

Therefore, there is need to improve the cannulas now used in connection with therapeutic gas administering systems.

More specifically, many known cannulas do not provide a location for mixing gases that is remote from a patient's nares. Such a remote mixing location can be advantageous for better control of the final mixture administered to the patient. Such a remote location can also be controlled without inhibiting a patient in any way. However, since known cannulas do not have such an element, they have disadvantages.

Still further, many known cannulas have designs that waste therapeutic gas. Further, many known cannulas cannot be used in a system that can precisely detect breathing patterns of a patient and cannot be used to precisely and accurately control dosage, concentration and flow rates of the gases.

Therefore, there is a need for a cannula that efficiently administers therapeutic gas to a patient in a manner that overcomes the drawbacks of known cannulas.

Still further, many systems that are used to administer therapeutic gas to a patient include primary gas sources in the form of pressurized cylinders. Some of these systems include a "flow direction" check valve downstream of the inlet to seal the system when the supply pressure is removed. However, a check valve system may have drawbacks if used in certain circumstances.

For example, when a pressurized source is exchanged, there exists the possibility that air will be trapped within the volume of the system plumbing that is exposed to air during the exchange. It is desirable to keep that volume of air as small as possible so the resulting trapped air volume is reduced. Any trapped air will degrade the quality of the high purity gases contained within the remainder of the system when intervening valves are opened. This degradation is proportional to the volume of trapped air. Therefore, it is desirable to maintain this dead volume to a minimum.

Furthermore, it is advantageous to provide a system sealing action as close to the supply inlet as possible to further minimize the dead space volume upstream of the sealing surfaces. A flow direction check valve is not able to achieve all of these goals. Therefore, there is a need for an equalizing valve that can minimize dead space volume.

It is noted that it is possible to flush or purge the system to remove contaminated gas from some dead space regions. However, for purging to be effective, the dead space must be substantially swept out during periods of gas flow. If there are poorly swept regions within the dead space, purging will have to be extended to allow for diffusion and other mechanisms to dilute the contaminated regions. Therefore, there is a need for a means for ensuring proper purging of a system used to administer therapeutic gas to a patient.

Furthermore, purging requirements are strongly dependent on the relative size of the contaminated volumes. Purging is often complicated in many situations due to possible toxic effects of the therapeutic gases; and the high cost of medical grade gases.

Therefore there is a further need for a valve that will make purging most efficient and effective while overcoming the just-mentioned problems.

It is also noted that an autonomous gas delivery system should be able to detect the supply pressure so when a pressurized cylinder has been attached and the supply valve opened, a control system is signaled. This requires suitable positioning of a pressure sensing element.

However, in order to maintain low dead space, a pressure sensor must be located on the downstream side of an inlet sealing mechanism. In the prior art, a simple back flow prevention check valve has provided this function. A check valve will seal when there is a lower supply pressure on the downstream side of the check valve. If the check valve seals, the pressure sensor, which is located further downstream of the check valve, will continue to show the pressure when the check valve is closed and will not indicate the actual supply pressure. If, subsequent to this, a supply is attached that is at a lower pressure than the "checked" pressure, the system will not be able to detect the connection.

Therefore, there is a need for a means for sealing a system such as disclosed herein which will be able to fully detect and control the flow of the system during changing of gas sources.

In general, it is desirable to close off the inlet of a system such as disclosed herein when a supply is detached and to maintain the inside of the high purity system at a positive pressure with respect to atmospheric pressure. By closing off the inlet, the chance of contamination is reduced. By maintaining a positive internal pressure, any small leaks that may be present will tend to leak in an outward fashion helping to prevent atomspheric gas from entering the system.

Therefore, there is a need for a means for connecting the system of the present invention to a source of gas that will reduce the possibility of contamination of the system.

OBJECTS OF THE INVENTION

It is a main object of the present invention to provide a system and elements for delivering NO to a spontaneously breathing, non-ventilated patient.

It is another object of the present invention to manage NO delivery to a spontaneously breathing, non-ventilated patient such that concentrated NO is as low as reasonably possible while delivering the desired amount of NO to the distal portions of the patient's lungs.

It is another object of the present invention to provide a system and elements for delivering NO to a spontaneously breathing, non-ventilated patient that is compatible with periodic, routine or continuous modes of operation.

It is another object of the present invention to provide a system and elements for delivering NO to a spontaneously breathing, non-ventilated patient that is easily used by patients, clinical staff and other caregivers with a wide and varying range of skills.

It is another object of the present invention to provide a system and elements for delivering NO to a spontaneously breathing, non-ventilated patient that is easily cleaned, purged and maintained.

It is another object of the present invention to provide a system and elements for delivering NO to a spontaneously breathing, non-ventilated patient that is easily monitored.

It is another object of the present invention to provide a system and elements for delivering NO to a spontaneously breathing, non-ventilated patient that has any limited lifetime elements thereof easily replaced.

It is another object of the present invention to provide a system and elements for delivering NO to a spontaneously breathing, non-ventilated patient which will minimize concentration of therapeutic gases delivered to any tissue that requires treatment.

It is another object of the present invention to provide a system and elements for delivering NO to a spontaneously breathing, non-ventilated patient which will accurately and efficiently deliver a desired concentration and dose to the patient.

It is another object of the present invention to provide a system and elements for delivering NO to a spontaneously breathing, non-ventilated patient which can be adapted for use with a cannula or a mask while still accurately and efficiently delivering desired doses and concentrations of therapeutic gases to the patient.

It is another object of the present invention to provide a system and elements for delivering NO to a spontaneously breathing, non-ventilated patient which can deliver any desired therapeutic gas or combination of gases to the patient in an efficient and effective manner.

It is another object of the present invention to provide a system and elements for delivering NO to a spontaneously breathing, non-ventilated patient which has alarms and alarm systems.

It is another object of the present invention to provide a system and elements for delivering NO to a spontaneously breathing, non-ventilated patient which includes locks to prevent undesired operation of the system or its elements.

It is another object of the present invention to provide a system and elements for delivering NO to a spontaneously breathing, non-ventilated patient which has means for providing system operational history.

It is another object of the present invention to provide a system and elements for delivering NO to a spontaneously breathing, non-ventilated patient which is adaptable to a wide variety of conditions and system requirements.

It is another object of the present invention to provide a system and elements for delivering No to a spontaneously breathing, non-ventilated patient which has means for delivering desired therapeutic gases even while a main source of gas is being replaced.

It is another object of the present invention to provide a system and elements for delivering NO to a spontaneously breathing, non-ventilated patient which is portable.

It is another object of the present invention to provide a system and elements for delivering NO to a spontaneously breathing, non-ventilated patient which is autonomous.

It is another object of the present invention to provide a system and elements for delivering NO to a spontaneously breathing, non-ventilated patient which can respond to changes in patient parameters such as breath rate and tidal volume.

It is another object of the present invention to provide a system and elements for delivering NO to a spontaneously breathing, non-ventilated patient which can respond to changes in environmental parameters.

It is another object of the present invention to provide a system and elements for delivering NO to a spontaneously breathing, non-ventilated patient which has a low transit time of gases through an entrainment cell.

It is another object of the present invention to provide a system and elements for delivering NO to a spontaneously breathing, non-ventilated patient which has an entrainment cell that is easily cleaned and maintained.

It is another object of the present invention to provide a system and elements for delivering NO to a spontaneously breathing, non-ventilated patient which has an entrainment cell that is not prone to clogging.

It is another object of the present invention to provide a system and elements for delivering NO to a spontaneously breathing, non-ventilated patient which has an entrainment cell that efficiently mixes gases.

It is another object of the present invention to provide a system and elements for delivering NO to a spontaneously breathing, non-ventilated patient which has an entrainment cell that can monitor flow rates.

It is another object of the present invention to provide a system and elements for delivering No to a spontaneously breathing, non-ventilated patient which has an entrainment cell that is spaced from a patient's face.

It is another object of the present invention to provide a system and elements for delivering NO to a spontaneously breathing, non-ventilated patient which has an entrainment cell with an efficient and effective geometry.

It is another object of the present invention to provide a system and elements for delivering NO to a spontaneously breathing, non-ventilated patient which has an entrainment cell with an entrainment cell that can be efficiently flushed during operation.

It is another object of the present invention to provide a system and elements for delivering No to a spontaneously breathing, non-ventilated patient which has an entrainment cell that is easily inspected.

It is another object of the present invention to provide a system and elements for delivering NO to a spontaneously breathing, non-ventilated patient which has an entrainment cell that has a total flow rate of gases during inspiration which is a large fraction of a patient's inspiratory flow rate.

It is another object of the present invention to provide a system and elements for delivering NO to a spontaneously breathing, non-ventilated patient which has an entrainment cell with a low dwell time of therapeutic gases as compared to the desired delivery flow rate.

It is another object of the present invention to provide a system and elements for delivering NO to a spontaneously breathing, non-ventilated patient which has a means for effectively and efficiently equalizing pressure between a source of pressurized gas and the system, but keeping the system pressurized slightly above atmospheric pressure if the gas source is removed.

It is another object of the present invention to provide a system and elements for delivering NO to a spontaneously breathing, non-ventilated patient that maintains dead volume to a minimum It is another object of the present invention to provide a system and elements for delivering NO to a spontaneously breathing, non-ventilated patient that includes an equalizing valve that can minimize dead space volume It is another object of the present invention to provide a system and elements for delivering NO to a spontaneously breathing, non-ventilated patient that includes a means for ensuring proper purging of a system used to administer therapeutic gas to the patient.

It is another object of the present invention to provide a system and elements for delivering NO to a spontaneously breathing, non-ventilated patient that includes a valve that will make purging most efficient and effective while overcoming the problems associated with the prior art.

It is another object of the present invention to provide a system and elements for delivering No to a spontaneously breathing, non-ventilated patient that includes a means for sealing a system such as disclosed herein which will be able to fully detect and control the flow of the system during changing of gas sources.

It is another object of the present invention to provide a system and elements for delivering No to a spontaneously breathing, non-ventilated patient that includes a means for connecting the system to a source of gas that will reduce the possibility of contamination of the system.

SUMMARY OF THE INVENTION

These, and other, objects are achieved by a system that administers therapeutic gas to a spontaneously breathing, non-ventilated patient which accurately manages and supervises the delivery of gas. The system dilutes a high concentration therapeutic gas to a lower concentration prior to delivering it to a patient for inhalation. The system delivers the gas via nasal prongs or via a mask. It effects this delivery without requiring a source of pressurized diluting gas such as from a pump or compressed gas cylinder. Dilution can be accomplished with room air of close to local atmospheric pressure. The system also allows supplemental oxygen to be added to the respiratory gases if desired and works with a pulsed delivery device.

The system also includes a special cannula that further improves the overall effectiveness of the system. The cannula has an entrainment cell that is sized and shaped to produce a gas transit time therethrough that is most effective to properly mix, dilute and deliver the therapeutic gas to the patient. The entrainment cell is also sized and shaped to inhibit clogging and can be transparent if desired to provide a visual indication of the inside of the cell. The entrainment cell has ports and other elements that are located and positioned to thoroughly mix the gas with room air in a manner that is most effective and efficient. Furthermore, one form of the entrainment cell includes flow sensors that can be used so gas administration is accurate and precise. The flow sensor can act as an interlock to help ensure that sufficient room air is entrained for adequate dilution. Other forms of the cell include check valves, baffles and other ports. The entrainment cell provides desired mixing control that is suitable for the accurate system and is located remote from the patient's nares whereby patient safety and comfort are enhanced. The cell also is closed except for the ports and thus gas is not wasted due to leakage. Flow sensors can also be used to transmit pressure signals from the patient's nose through the therapeutic gas lumen so the beginning of inspiration may be detected.

The entrainment cell can be used with a cannula or with a mask as desired.

The system of the present invention can deliver one or more therapeutic gases to a patient for inhalation and can dilute the therapeutic gas with room air prior to delivering the gas to the patient. The room air for dilution is entrained by the respiratory effort of the patient so no supplementary air source such as compressed air or an air pump is required. The total flow rate of gases in the device during inspiration, including entrained air, is a large fraction of the patient's inspiratory flow rate and the total flow rate of the gases in the device is equal to the sum of the flow rate of each therapeutic gas plus the flow rate of entrained air. One form of the invention delivers a low flow rate of nitric oxide during inspiration where the nitric oxide flow rate is very small compared to the inspiratory flow rate. In such a case, the flow rate of entrained air is a large fraction of the patient's inspiratory flow rate. The high fraction of inspired air flowing through the device is achieved in part by the geometry and size of an entrainment cell and associated elements. The geometry gives a low flow resistance in the air entrainment port, entrainment cell, outlet lumen and nasal prongs used in conjunction with the entrainment cell. The size of the nasal prongs is a factor in the resistance to flow around the prongs and into the patient's nose. A form of the invention that includes a mask allows an even greater fraction of the inspired gas to travel through the device.

The entrainment cell is small, lightweight and relatively unobtrusive and the dwell time of therapeutic gas in the cell is low compared to the desired delivery flow rate because of the size of the entrainment cell. One form of the device includes a check valve at the outlet of the therapeutic gas lumens and these lumens are usually small to limit the gas conductivity thereat. The entrainment cell also ensures proper turbulent mixing of the gases prior to delivery to the patient. The cell can also include a narrowing of flow paths near the outlet of the entrainment cell to increase the turbulence for improving mixing as gas leaves the cell.

One important performance characteristic of the therapeutic gas delivery system is its temporal response. The temporal response of the system depends partially on its geometry, one aspect of which is the mixing location for the therapeutic gas. In one embodiment, the therapeutic gas is mixed near the inlet end of the entrainment cell. In another embodiment, the therapeutic gas is mixed between a baffle in the entrainment cell and the outlet end of the cell. In yet another embodiment, the therapeutic gas is mixed near the patient. In connection with this, we define several temporal characteristics.

Cannula latency $T_c$ is the delay from therapeutic gas metering from the gas controller until the therapeutic gas reaches the patient.

Therapeutic lumen propagation latency $T_p$ is the delay for a flow rate to propagate from the metering valve in the gas controller to the outlet of the therapeutic gas lumen. This delay is very small in all cases relevant to the disclosed system and will be neglected.

Cell inlet latency $T_{ci}$ is the delay for a therapeutic gas to travel from a mixing region near the inlet end of the entrainment cell to the outlet lumen.

Cell baffle latency $T_{cb}$ is the delay for a therapeutic gas to travel from a mixing region between the baffle and the outlet end of the entrainment cell to the outlet lumen.

Near patient mixing latency $T_{np}$ is the delay for a therapeutic gas to travel from a mixing region near the patient to the patient.

Outlet lumen latency $T_o$ is the delay for gas to travel from the beginning of the outlet lumen at the entrainment cell to the patient.

The Cannula latency will depend on where the therapeutic gas is injected from the therapeutic gas lumen. If therapeutic gas is injected at the inlet end of the entrainment cell, then $$T_c \approx T_{ci} + T_o$$

If therapeutic gas is injected between the baffle and the outlet end of the entrainment cell, then $$T_c \approx T_{cb} + T_o$$

If therapeutic gas is injected near the patient, then $$T_c \approx T_{np}$$

Where approximations have been made because the therapeutic lumen propagation latency has been neglected.

A small cannula latency is established using the present invention. The cell inlet latency and cell baffle latency are made small by having a small entrainment cell internal volume compared to the volume of gas flowing through the cannula during inspiration. The outlet lumen latency is made small by keeping the outlet lumen internal volume small compared to the volume of gas flowing through the cannula during inspiration. The near patient mixing latency may be made arbitrarily small by making the mixing location as close to the patient as desired.

One form of the entrainment cell has an air inlet port located in an end wall thereof. This location of the air inlet port helps prevent blockage of the port. The location of a therapeutic gas lumen next to the air inlet port and parallel to the cell axis also helps prevent blockage.

One form of the entrainment cell is also designed to be flushed out with each patient breath. A combination of a small internal volume and flow design achieves this.

The entrainment cell is easy to clean as it has a fairly simple internal structure. The cell in one embodiment is transparent for easy inspection. One form of the entrainment cell includes a flow sensor that can be used to accurately ensure that sufficient air is entrained to properly dilute the therapeutic gas as well as to measure the inspiratory flow of the patient and to detect the beginning of inspiration. The flow sensor can also be used to control the pulse rate and size of the gas delivery system.

The small size of the entrainment cell reduces the low pass filtering effect (provides a better transient response). The entrainment cell transmits the waveform of the therapeutic gas to the patient with minimal distortion other than dilution. The flow rate of therapuetic gas injected from the therapeutic gas lumen may vary with time. The same waveform of therapeutic gas is delivered to the patient along with the room air and any other therapeutic gas with the system of the present invention. A low pass filtering effect exists due to the particular geometrical characteristics of the device such as the small diameter and the length of the gas lumens and the volume of the entrainment cell. A small entrainment cell volume and narrow lumens reduce the filtering effect.

Some forms of the entrainment cell include check valves on the air entrainment port or ports to prevent therapeutic gas from escaping from the cell even if the therapeutic gas flow rate is large. Thus, the desired amount of therapeutic gas reaches the patient.

Some forms of the entrainment cell have interlocks for connecting the cell to the remainder of the flow circuit.

The present invention also includes an equalizing valve that equalizes pressure in low dead volume conditions. The equalizing valve simultaneously satisfies a number of objectives and overcomes the problems associated with the prior art as discussed above.

The equalizing valve of the present invention satisfies the above-stated objects. The valve has inlet sealing surfaces within the valve fitting that engages a supply fitting of a source of pressurized gas at the closest possible location to the supply inlet. The remaining volume of the inlet is reduced by substantially filling that volume with a pin, leaving a thin annulus for gas to pass into the system. This geometry helps preserve the downstream gas purity and will significantly reduce the required amount of purge gas.

The valve of the present invention maintains a sufficient positive internal pressure to ensure that air does not migrate into the high purity gas regions. Furthermore, gas is not allowed to enter the high purity regions until a sufficiently high supply pressure is attached to the system. As an added safety feature, the valve of the present invention permits flow to automatically throttle itself at very high rates in the event of a massive leak.

BRIEF DESCRIPTION OF THE DRAWING FIGURE

FIG. 5 shows a nasal cannula used to administer NO to a patient in accordance with the teaching of the present invention.

FIG. 5A is a diluting cannula with two nasal prongs and adapted to administer two therapeutic gases to a patient.

FIG. 5C is a diluting cannula with two nasal prongs and adapted to administer two therapeutic gases with mixing near an upstream end of an entrainment cell.

FIG. 5D is a diluting cannula with two nasal prongs and adapted to administer two therapeutic gases with mixing of one therapeutic gas near a patient's nose.

FIG. 19 shows an alternative form of the system of the present invention in which the entrainment cell is located in a convenient location, behind a patient's ear.

DETAILED DESCRIPTION OF THE PREFERRED EMBODIMENT OF THE INVENTION

Other objects, features and advantages of the invention will become apparent from a consideration of the following detailed description and the accompanying drawings.

Overall System

Figure 1:
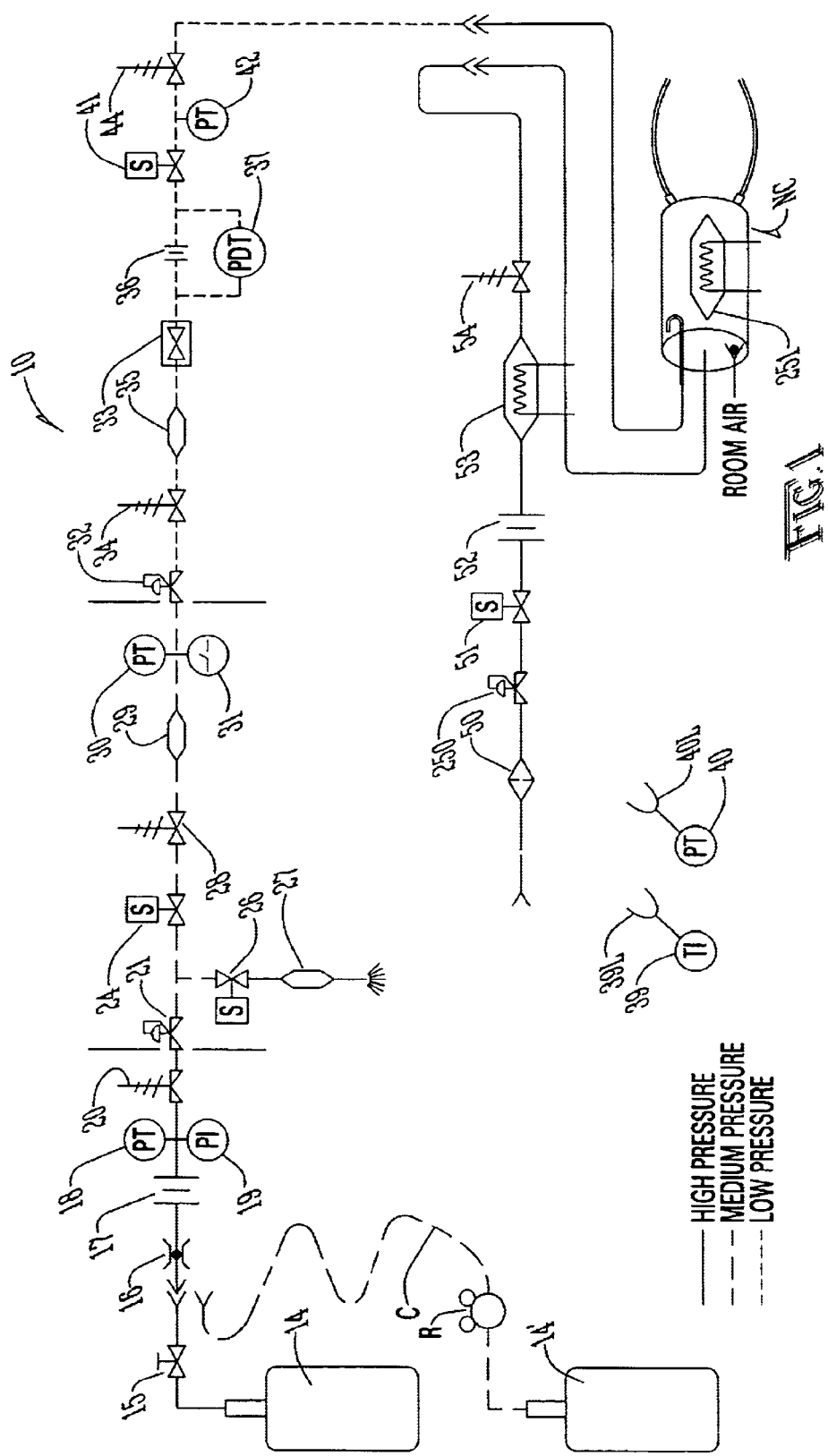
FIG. 1 is a schematic showing the overall system embodying the present invention.

Referring first to FIG. 1, a description of the overall system for administering therapeutic gas to a spontaneously breathing, non-ventilated patient will be described. It is noted that for reference, unless otherwise stated, the terms "upstream" and "downstream" will refer to a flow direction of gas from a source toward a patient. Other terms such as "inlet" and "outlet" will refer to the same flow direction. The overall system 10 is shown schematically and includes a source of first compressed gas 14 which is fluidically connected via a valve 15 and a pressure equalization valve 16 to a flow restrictor 17. Alternatively, a large source of gas 14' can be connected via a pressure regulator R which reduces the pressure and a flow conduit C to the inlet of the system. During normal operation of system 10, when a cylinder is connected, the pressure on the system side (i.e., downstream of valve 16) of valve 16 is equal to the cylinder pressure minus the equalization pressure (for example, 50 psi). When the cylinder is disconnected, a small amount of gas flows out of the cylinder side of the valve until the pressure on the system side of the valve reaches equalization pressure. This pressure is measured by a pressure sensor 18, with flow restrictor 17 being part of the equalization valve assembly. The pressure equalization valve/flow restrictor limits the maximum flow of the first gas in the case of a device failure. A pressure gauge 19 indicates cylinder pressure +/− the equalization pressure when a cylinder is connected. A burst diaphragm 20 is included for safety to vent if a cylinder is connected that is pressurized to greater than the rated inlet pressure of the system. A pressure regulator 21 reduces the pressure of the first gas from the cylinder pressure (+/− equalization pressure) to a desired level (for example, 100 psi). A solenoid valve 24 closes when system 10 is turned off or if a cylinder is disconnnected or is empty. Valve 24 seals the inlet side of the system to keep contaminants out when system 10 is off and to keep a reservoir from discharging through the inlet of the system when the cylinder is not connected. A purging solenoid valve 26 is fluidically connected to the system. When an adequately pressurized cylinder is connected and valve 15 is opened, a small amount of gas flows through pressure equalization valve 16 and the system side of valve 16 rises to the cylinder pressure minus the equalization pressure. This gas will contain some air that was trapped between cylinder valve 15 and equalization valve 16. Pressure sensor 18 detects the pressure rise and the system will know that a new cylinder has been connected. Solenoid valve 26 will be opened so gas from the cylinder flows through the inlet and the circuit upstream of valve 24. This gas flows out through muffler 27. If a large cylinder is connected, the medium pressure hose C and regulator R must also be purged so the purge duration will be longer. The user enters the cylinder size to indicate whether an extended purge is required.

At the end of the purge cycle, valve 26 is closed. The pressure at sensor 18 drops when valve 26 is opened and will rise when valve 26 is closed. If this does not occur, a proper purge was not carried out and the system is designed to include-control elements to respond accordingly. If pressure at sensor 18 rises to a high enough pressure, valve 24 will open. A pressure relief valve 28 is present for safety purposes and a reservoir 29 is located downstream of valve 24. Reservoir 29 is pressurized to the outlet pressure of regulator 21 (for example, 100 psi) during normal operation when a pressurized cylinder is connected. A pressure sensor 30 senses reservoir pressure and a pressure switch 31 switches at some pressure slightly above atmospheric pressure (for example, 5 psi). If switch 31 switches, it indicates that pressurization was lost in the reservoir and the system may have been contaminated. The system includes means for monitoring this switch at all times, even when the system is off. A pressure regulator 32 regulates to some pressure lower than regulator 21 (for example, 10 psi). It drops the pressure to an appropriate value for inlet of valve 33. When a source cylinder is disconnected or drops below an adequate pressure, this is sensed by sensor 18 and valve 24 is closed. The system will continue to deliver gas from the supply in reservoir 29. The reservoir pressure will begin to drop, but delivery will be unaffected as long as the presure remains high enough that regulator 32 can properly regulate. The system further includes means to monitor the reservoir pressure and calculate and indicate the remaining lifetime of reservoir 29.

A pressure relief valve 34 is for safety purposes. A small space 35 (e.g., 50 ml) is located downstream of regulator 32. This acts as a gas capacitor so that the pressure upstream of valve 33 does not fluctuate too much when valve 33 is operated. Valve 33 is a proportional control valve that meters the first gas flow to a patient. A differential pressure sensor 37 measures the pressure drop across an orifice 36 to determine the flow through valve 33. An ambient temperature sensor 39 and an ambient pressure sensor 40 generate signals connected to monitoring elements of the system by leads 39L and 40L. The signals are monitored by the system and used in calculations made by other elements of the system, such as computers or the like. The computing elements of the system are not shown but it is understood that such elements are included when and where necessary. The ambient temperature should be approximately equal to the temperature of the gas downstream of valve 33 under most conditions. Using ambient temperature, the pressures at pressure sensor 37 and sensor 40 and knowing the characteristics of orifice 36, the mass flow through valve 33 can be calculated. This flow may be used as a feedback to control valve 33. A solenoid valve 41 is closed when system 10 is off to keep the gas channel pressurized. A pressure sensor 42 is located to detect the patient's breath. When the patient inhales through their nose, the pressure in the nares drops. This pressure drop is transmitted through a nasal cannula NC to pressure sensor 42. When this pressure drops below a threshold value, the start of inspiration is indicated and delivery starts. Sensor 42 may also detect the pressure during expiration and this data may be used in delivery algorithms. It may also be possible to detect the start of inspiration using the flow sensor 251 to detect the flow of air in the entrainment cell which will occur with inspiration.

It is understood that the feedback loops and circuits as well as the signal generators, signal receivers and signal processors for pressure, temperature and flow measurements as well as valve actuators and various detectors used in the system use electrical circuits that are not shown, but are included as required. By way of example, block diagrams of such circuitry and control elements are shown in FIGS. 18A–18F. These circuits and elements are used when functions are mentioned herein with reference to operation of system 10.

A pressure relief valve 44 protects the patient. If the pressure at valve 44 is too high, valve 44 will vent. Cannula NC is connected downstream of valve 44. When a breath is detected, valve 33 opens to deliver the desired gas pulse. The gas flows into a first gas lumen of cannula NC. Mixing and dilution proceed as described below. The second gas source is a medium pressure source (for example 20 to 50 psi) such as a pressure regulated cylinder or gas from a hospital wall source. The second gas channel is much simpler than the first and includes a filter 50 and a pressure regulator 250 that regulates pressure of a second gas to some low pressure (e.g., 2 psi), solenoid valve 51, a flow restrictor 52 and a flow sensor 53. When a pulse of the second gas is to be delivered, valve 51 is opened and gas flows. The flow rate is set by flow restrictor 52 and dosage is adjusted by adjusting the duration of the pulse. Flow sensor 53 senses flow to verify that flow is present and approximately of the correct magnitude. A pressure relief valve 54 protects the patient by venting if the pressure is too high. The second gas channel is fluidically connected to cannula NC downstream of pressure relief valve 54.

Figure 2:
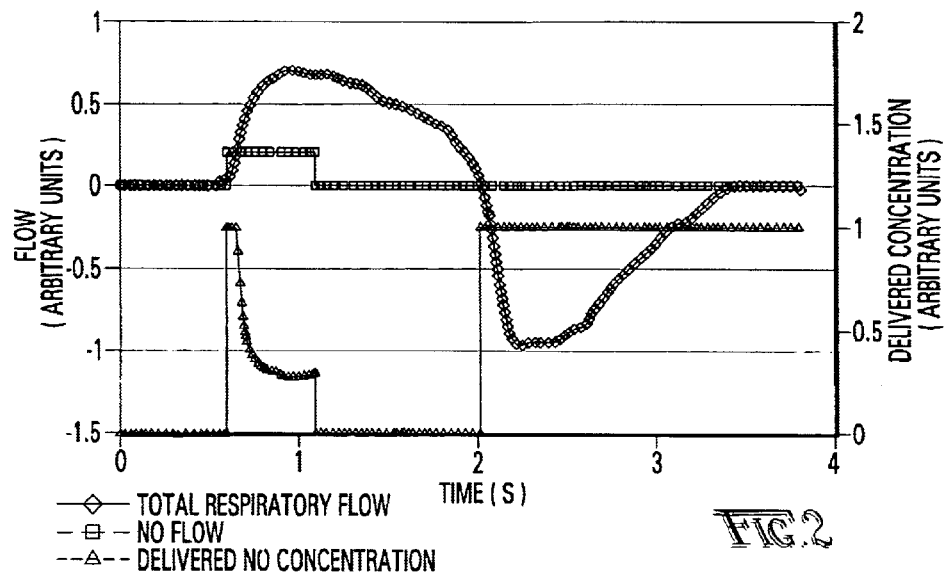
FIG. 2 is a flow versus time curve showing a rectangular pulse delivery.
Figure 3:
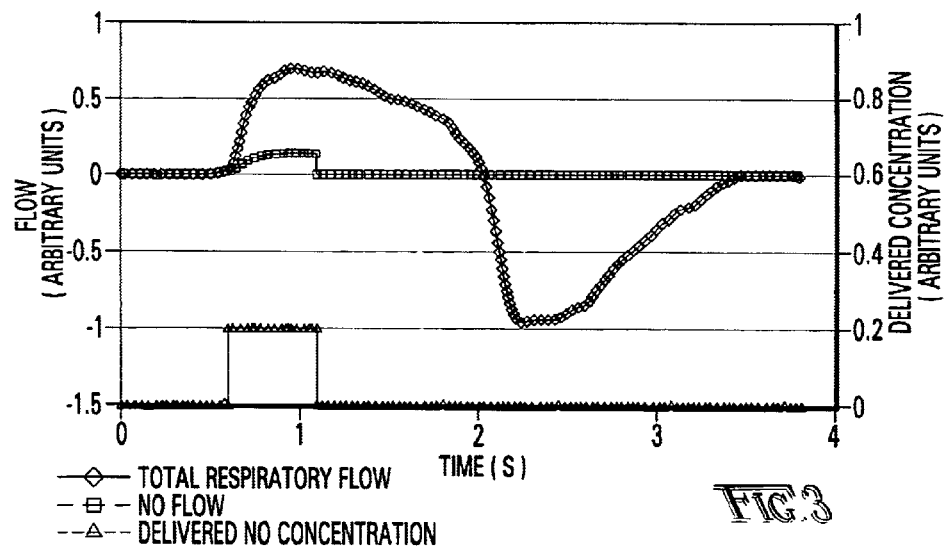
FIG. 3 is a flow versus time curve showing a pulse delivery with delivered gas flow rate proportional to inspiratory flow rate.
Figure 4A:
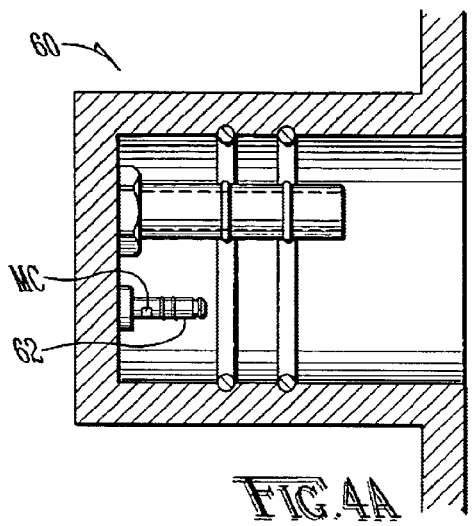
FIGS. 4A–4D show a connector for connecting an electrical circuit and therapeutic gas to an entrainment cell embodying the present invention.
Figure 4B:
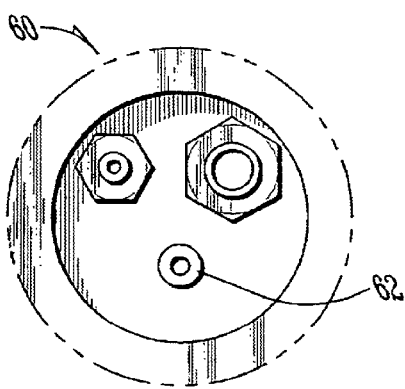
Figure 4C:
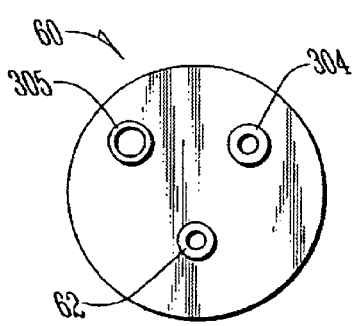
Figure 4D:
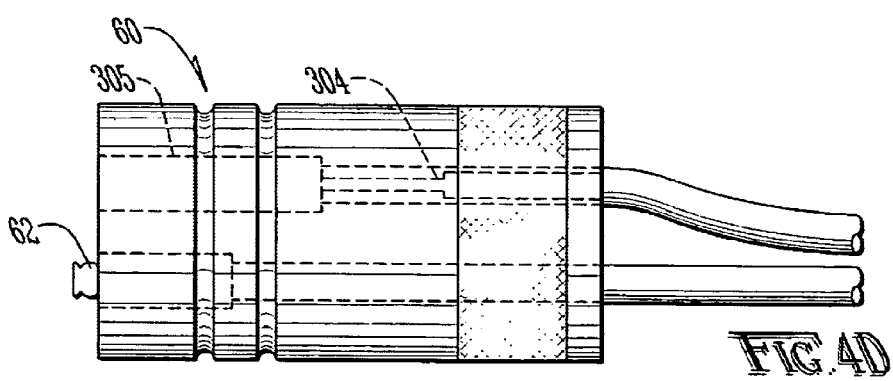

As discussed above, the system embodying the present invention can deliver customized pulses of a first and/or a second gas to the patient during inspiration. The shape of the gas pulse (flow rate versus time) of the first gas may be -approximately arbitrary and with system 10, many pulse shapes are possible. This opens up many possibilities for gas delivery to a patient. FIG. 2 shows a typical respiratory waveform along with a rectangular delivery pulse. The resultant concentration of the delivered gas when it is mixed with the respiratory gas is also shown. FIG. 3 shows the respiratory waveform along with a customized gas delivery pulse. The pulse has been tailored to have a flow rate that is proportional to the respiratory flow rate during the pulse. This results in a constant delivered gas concentration after mixing. Many pulse shapes are possible and the shape and size may be determined by different methods as will occur to those skilled in the art based on the teaching of this disclosure. The pulse shapes may be predetermined and programmed into the system 10. For example, pulse flow rate can be proportional to the respiratory flow rate in a typical breath to give a constant concentration over the duration of the pulse. This concentration is the concentration after the delivered gas is diluted by the other inhaled gases.

Another example includes setting pulse timing so gas is delivered during a desired part of the breath. This results in gas delivery to a desired part of the respiratory tract.

Yet another example includes varying pulse amplitude during different parts of the breath so different amounts of gas are delivered to different parts of the respiratory tract.

Using system 10, the breath waveform (inspiratory flow rate versus time) may be monitored and an algorithm may be used that is based on inspiratory flow rate to determine the delivered flow rate.

Also, using system 10, the frequency of breathing may be monitored and the delivered flow rate may be determined from an 0 algorithm that is based on the breath frequency.

As discussed above, delivery algorithms are possible that adjust gas delivery. The delivery may be adjusted based on measured patient parameters or environmental parameters.

For example, a constant concentration delivery on a large v time scale is possible using system 10. The concentration of the delivered gas during a pulse, after dilution by the other inhaled gases, is kept constant on a time scale of several breaths. The delivered flow rate is adjusted so that it is proportional to the respiratory flow rate. The respiratory flow rate might be directly measured or inferred from changes in other respiratory parameters such as breath rate.

Yet another algorithm includes a constant concentration delivery on a small time scale. In this situation, the concentration of the delivered gas during a pulse, after dilution by other inhaled gases, is kept constant over the duration of a pulse. The delivered flow rate is adjusted so that it is proportional to the respiratory flow rate. The respiratory flow rate might be measured in real time to accomplish this.

Still another algorithm includes delivery during a constant fraction of inspiration. In this algorithm, as breath rate changes, the duration of inspiration also changes. The pulse length could be altered to be proportional to the inspiratory time. For example, the pulse could be on during the first third of inspiration regardless of the duration of inspiration.

Still another algorithm includes constant time dosage delivery. In this situation, delivery is adjusted so that the total amount of delivered gas/time remains constant over a long time scale. If the breath rate increases, the amount of gas delivered during each breath is decreased.

As discussed above, system 10 includes an internal reservoir for uninterrupted service. The reservoir contains a quantity of gas so the system can continue to deliver gas to the patient while the source gas cylinder is being replaced. The reservoir is recharged when a new source cylinder is connected. Uninterrupted gas delivery is important for certain applications such as inhaled nitric oxide therapy.

System 10 is also amenable to use with multiple cylinder sizes as well as to use with either a cannula or a mask. Still further, cannula NC can include a diluting device to dilute the first and/or second gas with room air before they are delivered to the patient. This will be further discussed below. A diluting mask can also be used and will dilute the first and/or second delivered gas with room air before they are delivered to the patient's nose or mouth.

In addition to the above-discussed advantages, system 10 is amenable to maintaining the first gas channel inside the system clean. The first gas channel is kept pressurized above atmospheric pressure so that contaminating gas does not enter from the environment. When system 10 is turned off, it automatically seals the first gas channel and monitors the pressure to ensure that it does not drop below a predetermined pressure.

System 10 also includes alarms that warn of dangerous or undesirable situations, such as apnea, cannula/mask disconnect, system malfunction, gas cylinder low or empty, poor dilution by the cannula or mask, battery low or exhausted, compromise of gas channel pressurization, or the like. These alarms are monitored and recorded as necessary.

A cannula connector 60 is shown in FIGS. 4A–4D and ensures proper connection of gas to the nasal cannula or mask. Connector 60 includes an electrical interlock plug 62 that senses if the gas conduits are properly connected. The plug is designed to indicate disconnection of gas conduits 304, 305 before gas connection is actually broken. The connector may also include a means MC to indicate the type and characteristics of the device. This means could be a built-in memory chip, resistor, or other means. These means are not shown in FIG. 4 for the sake of simplicity.

System 10 can also be adjusted to account for temperature and/or pressure changes. As discussed above, system 10 measures ambient pressure and temperature and can adjust gas delivery to the patient based on these parameters and the desired algorithm.

System 10 also monitors battery charging and discharging for any battery used in system 10. System 10 also includes means for calculating battery capacity and remaining life according to means and methods known to those skilled in the art. Batteries may be charged during continued use of the system.

System 10 also includes subsystems that automatically run self-diagnosis tests at selected times. These subsystems can also record system operation. Patient data may be logged and recorded in like manner.

System 10 includes several features that reduce the generation of nitrogen dioxide if the first delivery gas is nitric oxide. Nitric oxide spontaneously reacts with oxygen to produce nitrogen dioxide which is toxic. The reaction rate is proportional to oxygen concentration and time and to the square of nitric oxide concentration. Oxygen is minimized in most of the first gas channel by keeping the channel pressurized, automatic purging and by having a small dead space. Automatic purging also removes oxygen and nitrogen dioxide from the outlet when delivery is started. The dwell time when nitric oxide and oxygen are mixed is minimized by mixing nitric oxide with air or oxygen in the cannula relatively close to the patient's nose and by sweeping the mixed gas out of the cannula with every breath.

System 10 may also be capable of decreasing bioeffects. NO can cause adverse bioeffects in high concentrations and possibly after extended exposure to lower concentrations. To decrease the probability of adverse bioeffects, it is desirable to minimize the NO exposure required to achieve desired therapeutic effects. As mentioned above, $NO_2$ generation is proportional to the square of the NO concentration. Adverse bioeffects due to NO could also be nonlinear. A doubling of the NO concentration might cause more than a doubling of adverse bioeffects. If this is the case, it may be desirable to keep the NO concentration constant over the pulse duration. The ability of system 10 to deliver a custom NO pulse shape allows this to be done.

Cannula

Figure 5B:
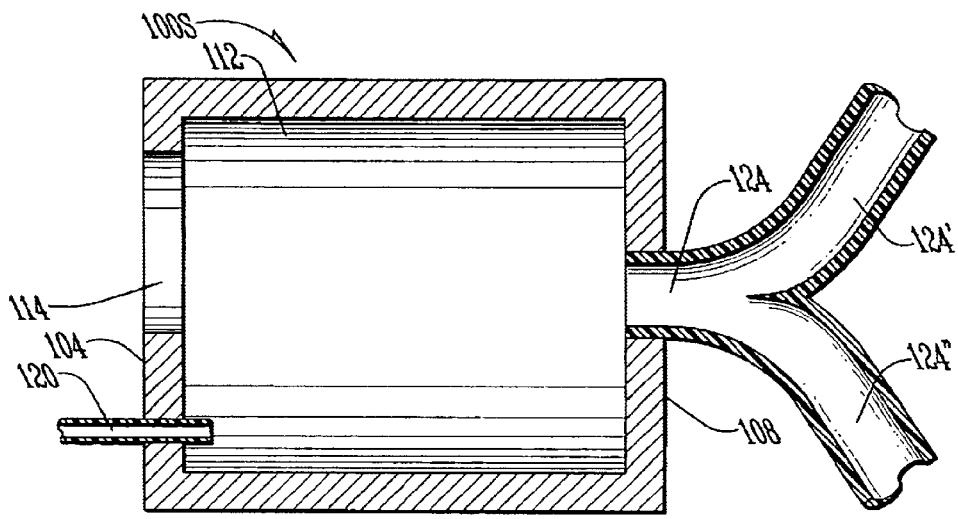
FIG. 5B is a short entrainment cell used in conjunction with the system embodying the present invention.

A cannula NC is shown in FIG. 1. Referring now to FIG. 5, a preferred form of the cannula will be discussed. Cannula 70 dilutes therapeutic gas to a safe level using room air that is entrained into the cannula by the patient's own breathing, eliminating the need for a separate diluent gas source. As will be understood from the teaching of the following disclosure, cannula 70 also incorporates a means for measuring the flow in the cannula to allow for the verification that therapeutic gas is being sufficiently diluted. The flow measurement means might also be used to detect the inhalation of the patient and time the delivery of the therapeutic gas or gases.

Referring to FIG. 5, cannula 70 includes a gas connector 72 that is fluidically connected to a first controlled source of therapeutic gas, a lumen 74 that conducts the first therapeutic gas from its source to an entrainment cell 75, a gas connector 76 that fluidically connects a second source of gas that may be a second therapeutic gas or a diluent gas to a second lumen 78 that conducts the second gas from its source to entrainment cell 75, an electrical connector 80 that connects electrical wires 82 to an electrical circuit, a lumen 84 through which the electrical wires are fed, a flow sensor 86 is positioned in entrainment cell 75, a check valve 88 is located on entrainment cell 75 and through which room air may be entrained into entrainment cell 75. A lumen 90 is fluidically connected at one end thereof to an outlet end of entrainment cell 75 to receive gas therefrom and at the other end to nasal prongs 92, gases flow through lumen 90 to nasal prongs 92 which deliver the gases to the patient's nose.

Figure 6:
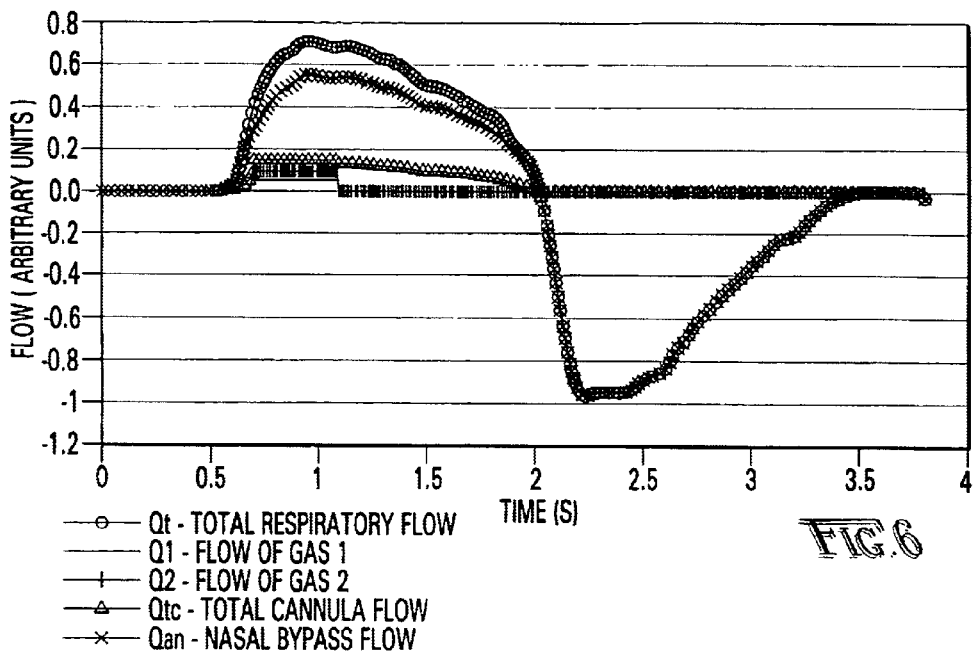
FIG. 6 is a flow versus time curve of various flows in the cannula and nose when the second therapeutic gas flow $Q_2 \neq 0$.

When the patient inhales, gases are drawn into the respiratory system at a total respiratory flow rate $Q_t$. At some time during inhalation, when $Q_t > 0$, the flow of therapeutic gas $Q_1$ and therapeutic/diluent gas $Q_2$ is turned on. Sample flow rates are shown in FIG. 6. $Q_1$ and $Q_2$ are not necessarily coincident. The total respiratory flow $Q_t$ is supplied by the total air flow in the cannula ($Q_{tc}$) plus the air flow entrained from the room and entering the nose around nasal prongs 92 ($Q_{an}$).

$$Q_t = Q_{tc} + Q_{ac}$$

The fraction (K) of the total respiratory flow that flows through the cannula is:

$$K = Q_{tc}/Q_t$$

K and $Q_{tc}$ are minimum when $(Q_1+Q_2)$ is minimum and increase as $(Q_1+Q_2)$ increases. The total cannula flow $Q_t$, is made up of $Q_1$, $Q_2$, and air that is entrained into the flow entrainment cell 75 through the check valve 88 ($Q_{ac}$).

$$Q_{tc} = Q_1 + Q_2 + Q_{ac}$$

Where $Q_2=0$. The concentration of the first therapeutic gas entering the patient's nose from cannula 70 ($C_{1c}$) depends on the concentration of the therapeutic gas source ($C_1$) and the flow rates as follows:

$$C_{1cmax} = C_1 \times Q_1/Q_{tc} = C_1 \times Q_1/(Q_1+Q_{ac})$$

Figure 7:
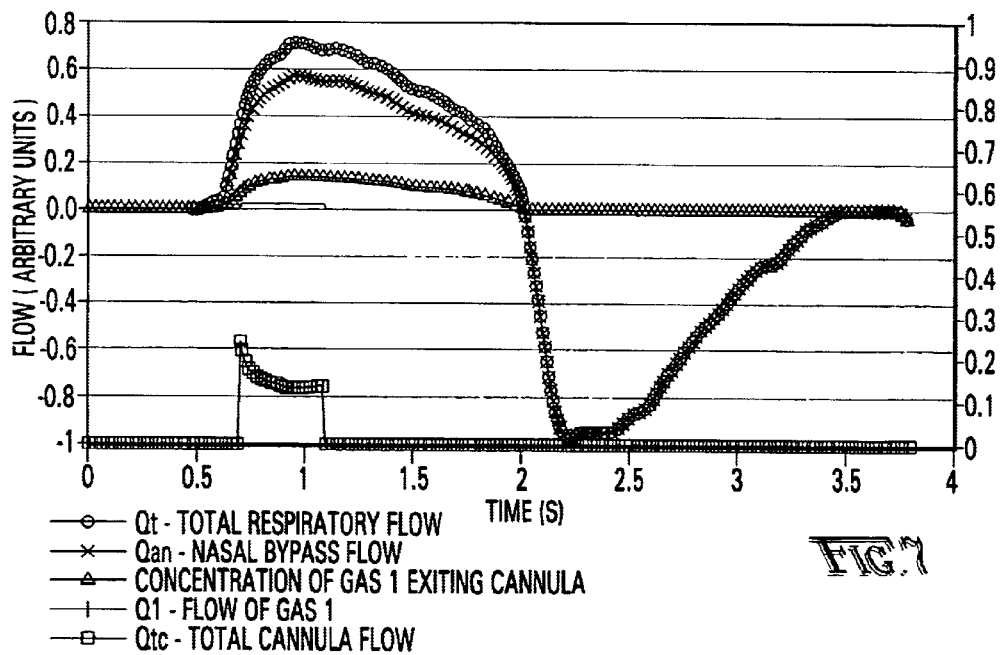
FIG. 7 is a flow vs time curve of various flows in the cannula and nose and a curve of the concentration of gas wxiting the cannula when the second therapeutic gas flow $Q_2=0$.

FIG. 7 shows the flow rates and the concentration of the therapeutic gas coming out of the cannula for the case where $Q_2=0$.

Flow sensor 86 measures $Q_{tc}$. If $Q_1$ $Q_2$ and $C_1$ are known, then $C_{1c}$ can be calculated to verify that it stays at a safe level. The measurement of $Q_{tc}$ may also be used to detect when the patient is inhaling and time the delivery of the first and second gases.

Figure 8:
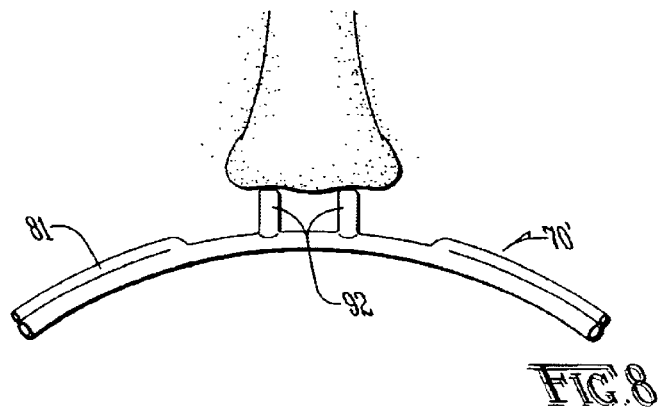
FIG. 8 is a nasal cannula with mixing near the nose.

FIG. 8 shows a variation of the cannula and is indicated at 70' in which a first therapeutic gas 81 is not mixed with $Q_2+Q_{an}$ until very near the nasal prongs. This has two possible advantages. The time that gas 81 is mixed with the second gas and the entrained air is reduced. This will reduce the reaction of gas 81 with the second gas and air if this reaction time is dependent. This may be important for a gas such as nitric oxide which reacts with oxygen to produce the toxic gas nitrogen dioxide. The reduced transit time of the mixed gas from the mixing point to the nasal prongs also means that the mixed gas will reach the patient sooner after the beginning of $Q_1$. This may be important in a situation such as when $Q_1$ is triggered by the detection of inhalation. Gas 81 can be delivered to the patient sooner after the beginning of inhalation. The flow sensor now measures $(Q_2+Q_{an})$ but $C_{1c}$ can still be calculated if $Q_1$ is known.

By way of completeness, it is noted that the following table presents reference breathing parameters which can be considered for the above relationships.

Reference Adult Breathing Parameters
   Tidal volume→250–500 ml
   Breathing frequency→10–15 breaths/min
   Peak inspired flow rate→30–60 l/min
   Inspiration period→0.75–1.25 s.
Reference Child Breathing Parameters
   Tidal volume→100–300 ml
   Breathing frequency→30–50 breaths/min
   Peak inspired flow rate→30–60 l/min
   Inspiration period→0.75–1.25 s.
Reference Neonatal Breathing Parameters
   Tidal volume→5–40 ml
   Breathing frequency→30–50 breaths/min
   Peak inspired flow rate→30–60 l/min
   Inspiration period→0.2–0.75 s.

Specifically, the cannula embodying the present invention includes an entrainment cell 75 shown in FIG. 5 which is sized and configured to provide a low temporal latency for gases flowing through entrainment cell 75. The low temporal latency, that is, the low dwell time for gases passing through the entrainment cell, reduces the time for those gases to react with each other. It also permits proper concentrations to be ensured.

Figure 9:
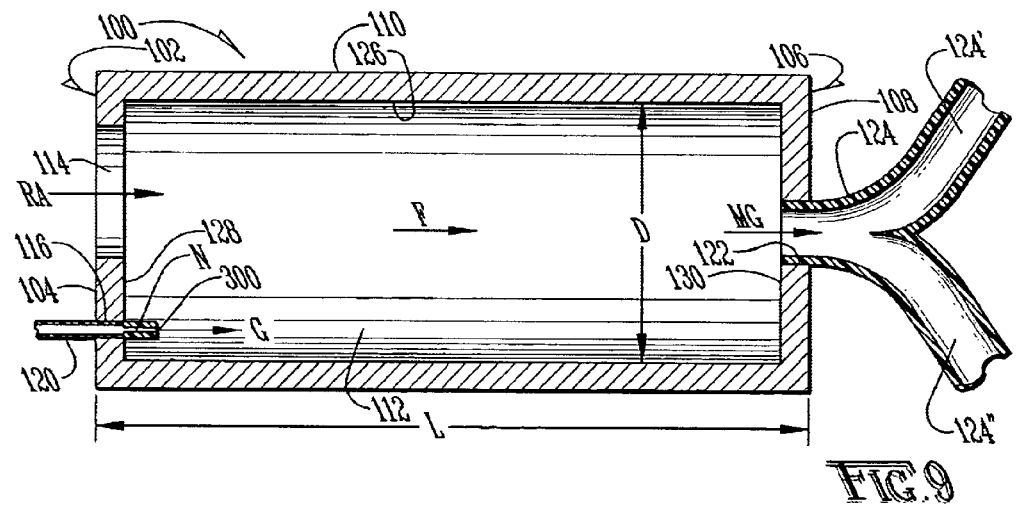
FIG. 9 is an entrainment cell used in the system embodying the present invention.

Referring to FIG. 9, an entrainment cell 100 is shown as including an inlet end 102 having an inlet end wall 104 and an outlet end 106 having an outlet end wall 108 connected together by a sidewall 110. Entrainment cell 100 is hollow and has an internal volume 112 into and out of which gases flow one form of the entrainment cell has an internal volume of less than 10 $cm^3$. An air inlet port 114 is defined through inlet end wall 104 and a therapeutic gas inlet port 116 is also defined through inlet end wall 104. As will be understood, the terms "inlet," "outlet," and the like are to be interpreted in terms of the flow direction of gases passing into, through and out of entrainment cell 100 during administration to a patient via a cannula, such as cannula NC or cannula 70. A gas flow direction F is indicated in FIG. 9 for reference.

The internal area of lumen 120 can be narrowed at its outlet 300 to area N as indicated in FIG. 9. This reduces the flow conductivity of the lumen at this point. This may reduce the diffusion of gases back into the lumen from beyond the lumen outlet when the gas flow in the lumen is off. This will reduce pollution of the therapeutic gas in the lumen. The narrowing of the lumen outlet is shown on cell 100 but can be used in connection with any of the entrainment cell forms discussed herein.

A therapeutic gas lumen 120 is fluidically connected at one end thereof to a source of therapeutic gas, and at the other end thereof to the interior volume 112 of entrainment cell 100 for conducting the therapeutic gas into the entrainment cell. Air inlet port 114 is fluidically connected on one side thereof to room air and on the other side thereof to interior 112 volume of entrainment cell 100 to conduct room air into interior volume 112. An outlet port 122 is defined through outlet end wall 108 and is fluidically connected at one side thereof to interior volume 112 to receive gases from interior volume 112. An outlet lumen 124 is mounted in outlet port 122 to have one end thereof fluidically connected to interior volume 112 and is fluidically connected to an exit end (not shown in FIG. 9, but see FIG. 5) to a patient's nose for conducting gases from interior volume 112 to the patient. Outlet lumen 124 can have two branches if suitable, such as branches 124' and 124".

Preferably, entrainment cell 100 is cylindrical with a length dimension L measured inside entrainment cell along inside surface 126 of sidewall 110 from inside surface 128 of inlet end wall 104 to inside surface 130 of outlet end wall 108 that is about two to three times the internal diameter D of entrainment cell measured between the inside surface 126 of sidewall 110 across the end walls.

Room air flows through air inlet port 114 as indicated by arrow RA and is entrained with gas flowing into the entrainment cell from lumen 120 as indicated by arrow C. These gases mix in interior volume 112 and flow out of entrainment cell 100 via lumen 124 as indicated by arrow MG. Air inlet port 114 is sized to provide sufficient room air to establish the proper mix in cell 100 for the flow rate of the therapeutic gas.

The indicated flow directions are for the case of inspiration when MG>G. During expiration, some or all flow directions may be reversed. If MG<G, gas may flow out of the cell through air port 114.

By way of example, the dimensions of the cannula device embodiment shown in FIG. 5 are as follows (all dimensions are approximate).
Gas lumens (one is shown in FIG. 9, but a plurality of lumens can be used if desired as will be understood from the following disclosure):
  inside diameter→0.1–0.5 cm
  length→180 cm
Outlet lumen (assuming that the outlet lumen splits when exiting the entrainment cell as shown in FIG. 9):
  inside diameter→0.5–0.8 cm
length from entrainment cell to nasal prongs or mask→20–40 cm entrainment cell:
  inside diameter, D→1.0–2.5 cm
  length, L→2–5 cm.
Air Inlet Port:
  area→0.7 cm
Nasal Prongs
  inside diameter→0.5 cm
  outside diameter→0.64 cm.

The preferred cannula latency is less than 100 ms with a fraction of inspired air flowing through the cannula being between 20% to 56% with the nasal prong embodiment. Various embodiments of the cannula will have different cannula latencies. Another embodiment of the cannula device is shown in FIG. 19. In this embodiment the entrainment cell is closer to the patient's nose, so the outlet lumen latency is decreased. There may be a single entrainment cell on one side of the nasal prongs, or the device may be symmetrical with an entrainment cell on each side. To decrease cell latency, a shorter entrainment cell, such as cell 100S shown in FIG. 5B can be used.

Some entrainment cells include one therapeutic gas lumen. As discussed above, more than one therapeutic gas can be administered to a patient, and thus a plurality of lumens can be included. This is indicated in FIGS. 5C and 5D. The lumen shown in FIG. 5D will be further discussed below.

Figure 10:
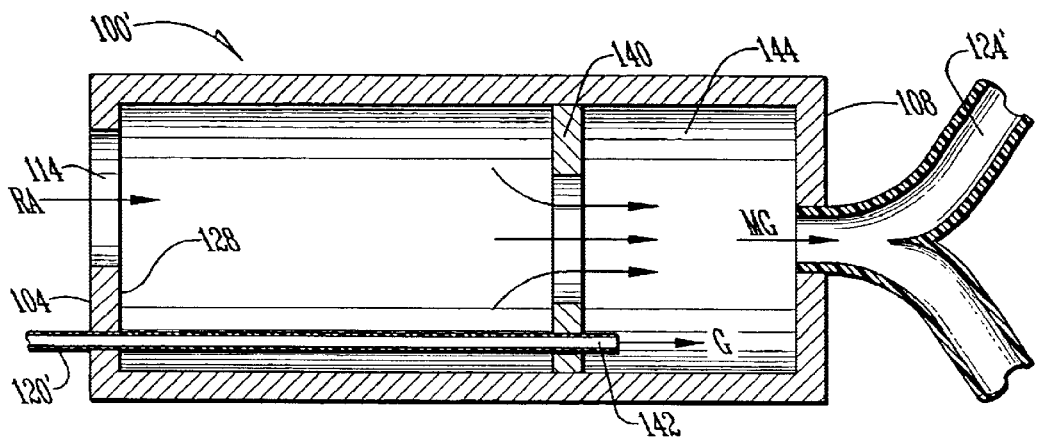
FIG. 10 is an alternative form of an entrainment cell having a baffle.

Another version of the entrainment cell is shown in FIG. 10 as entrainment cell 100'. Cell 100' includes a baffle 140 to create further turbulence in the gases flowing through cell 100'. As can also be seen in FIG. 10, cell 100' further includes a gas inlet lumen 120' extending from inlet end wall 104 past baffle 140 with an outlet end 142 located downstream of baffle 140 in a secondary mixing area 144. Room air enters cell 100' through air inlet port 114 and passes through baffle 140 into secondary mixing area 144 to be mixed with the therapeutic gas exiting inlet lumen 120'. The baffle increases turbulent flow in the cell and tends to enhance mixing of the gases as well as provides structural support to the cell. The baffle also tends to increase the pressure drop across the cell during inspiration. This may be helpful when detecting breath by the pressure drop at the start of inspiration. In the preferred embodiment, the baffle has an inside diameter of approximately 0.9 cm.

Figure 20:
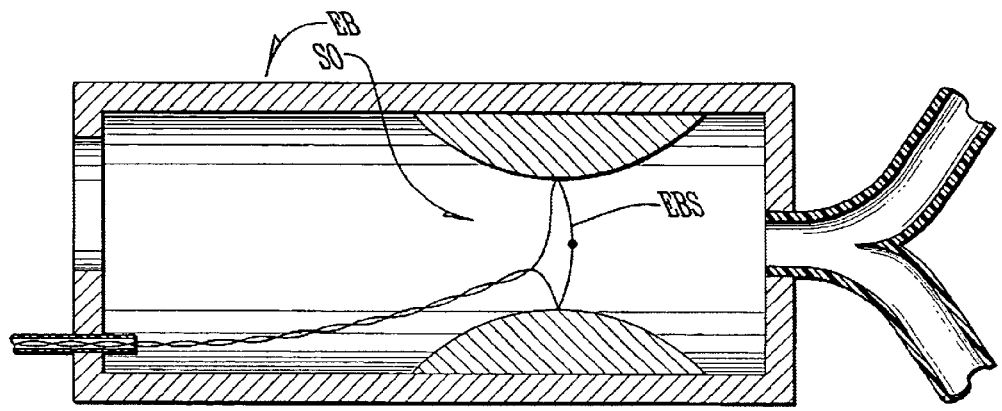
FIG. 20 shows an alternative form of the present invention in which a shaped orifice is located inside the entrainment cell.

In another embodiment shown in FIG. 20, a shaped orifice 50 is used in place of the baffle. This has the advantage that the flow at various points across the inside of the orifice will be more uniform. This may allow more accurate flow measurement. In addition, the pressure drop across the orifice will be smaller for a given flow velocity through the orifice compared to the baffle. This reduced flow resistance will help a large fraction of the inspired gases travel through the entrainment cell.

In all embodiments, room air is drawn into the entrainment cell by patient inhalation and this room air dilutes the therapeutic gas when it mixes with that gas. The air inlet port is sized to regulate the pressure in the cell to around atmospheric pressure which tends to aid metering of the therapeutic gas that is injected into the cell. The air inlet port is located in end wall 104 adjacent to the gas inlet lumen which tends to sweep gas out of the cell. Also, the end wall position of the air inlet port tends to reduce the likelihood of the port being blocked by external objects. The air inlet port is sized to be large enough to present only a small restriction to air flow through it and to properly meter air flow into the cell.

The air inlet port is shown as being circular, but could be other shapes as well, including, but not limited to, kidney shaped, oval, or the like.

Figure 11:
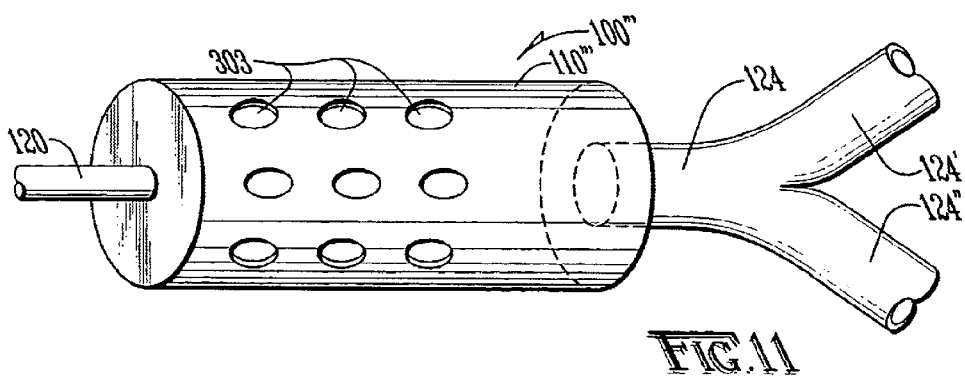
FIG. 11 is an alternative form of an entrainment cell having a plurality of air inlet ports.

A further embodiment of the entrainment cell is shown as entrainment cell 100''' in FIG. 11 and includes a plurality of air inlet ports 303 defined through side wall 110''' of cell 100'''. The sidewall located air inlet ports are large enough in total flow area (that is the combined flow areas of all ports) to present only a small flow restriction to entrained air. Again, while the ports 303 are shown as being circular, other shapes can also be used without departing from the scope of the teaching of this disclosure.

Figure 12:
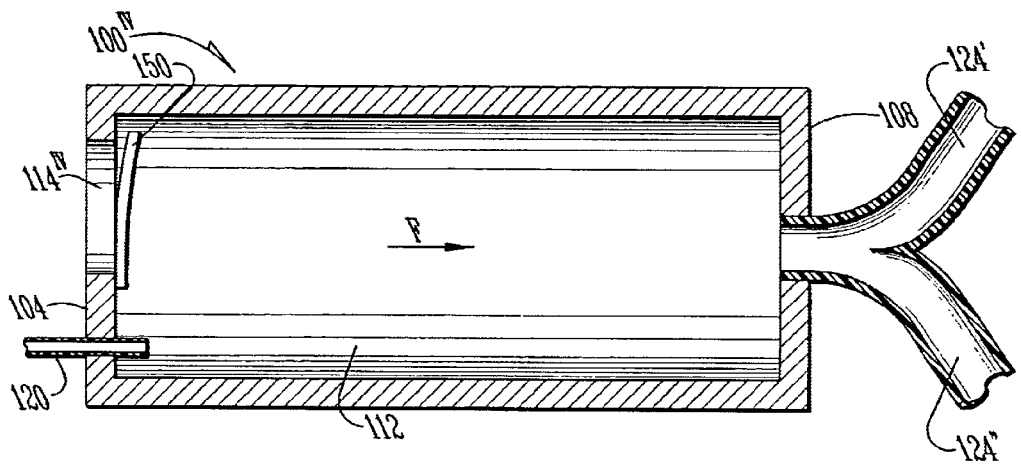
FIG. 12 is an alternative form of an entrainment cell having a check valve mounted to control air flow through an air inlet port.

Yet a further embodiment of the entrainment cell is shown in FIG. 12 as entrainment cell 100$^{IV}$ which includes a check valve 150 over air inlet port 114$^{IV}$. Check valve 150 permits room air to flow into the interior of entrainment cell 100$^{IV}$ but occludes the inlet port against backflow of air out of the interior of the cell. The check valve 150 improves the cleanliness of the entrainment cell by reducing the possiblity that foreign material, as well as exhaled gases, can reach the interior of the cell. The check valve also provides a half wave rectification of a flow signal and prevents the escape of therapeutic gas from the entrainment cell. Each of the air inlet ports 303 of entrainment cell 100''' can include a check valve similar to check valve 150 if desired.

Figure 13A:
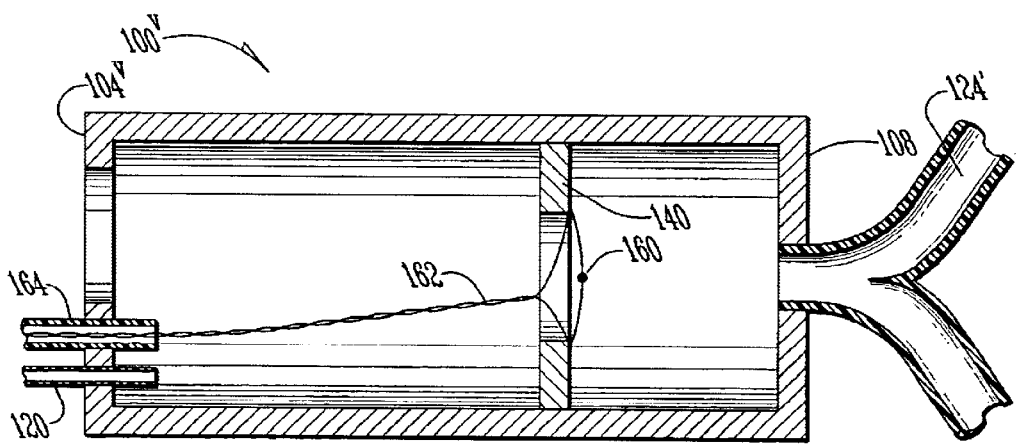
FIGS. 13A and 13B are alternative forts of an entrainment cell having a flow sensor.
Figure 13B:
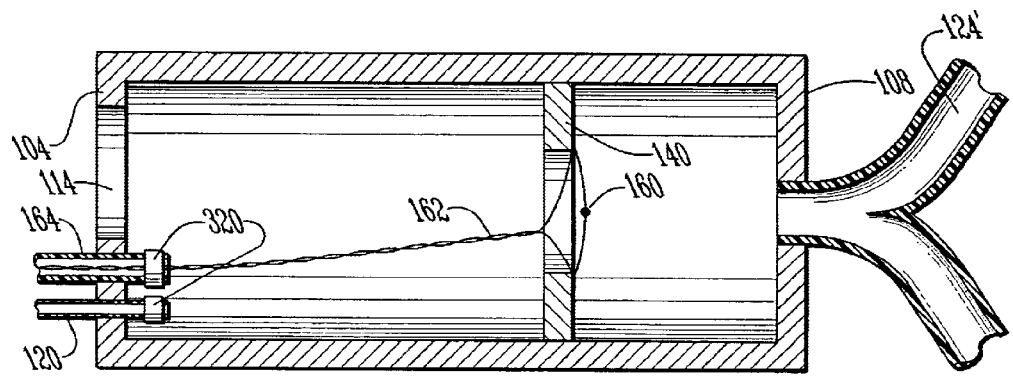
Figure 13C:
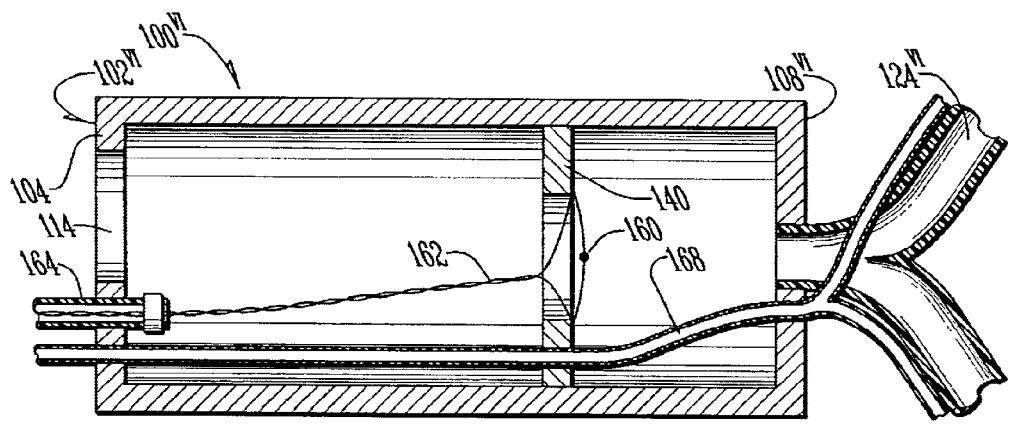
FIG. 13C is an alternative form of an entrainment cell having a lumen for directing gas to a mixing region near the patient.
Figure 14A:
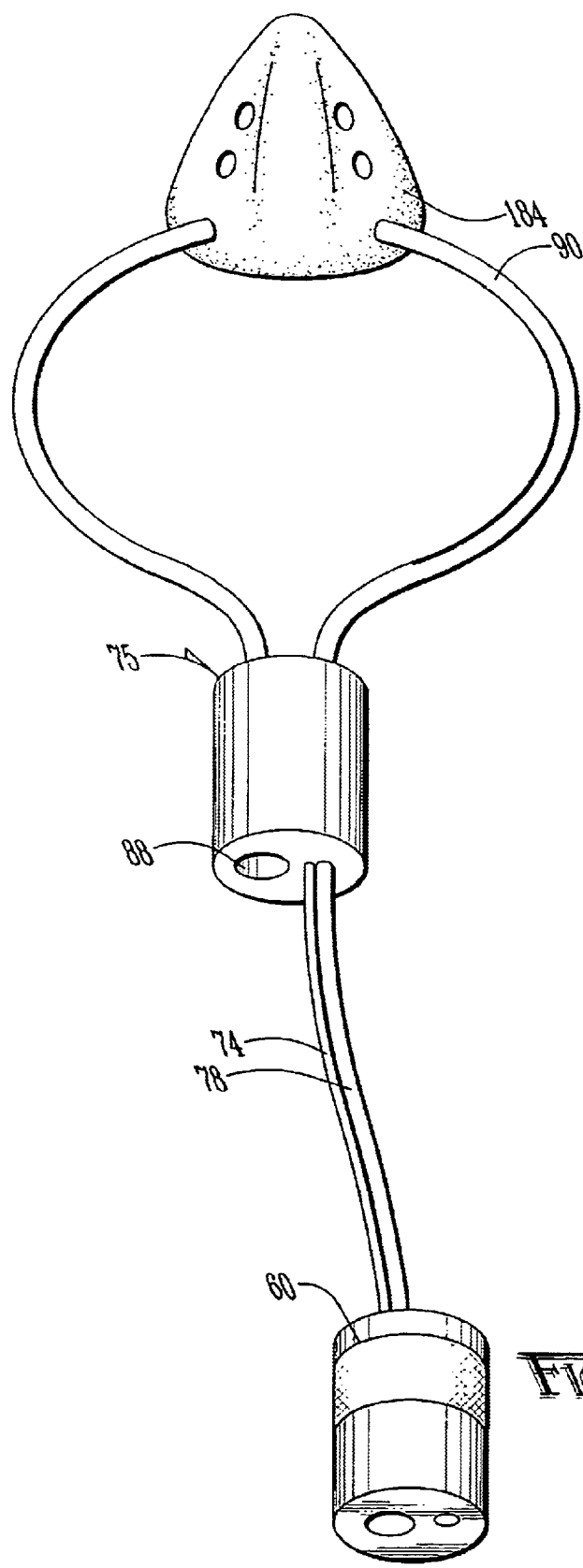
FIGS. 14A–14D show an alternative form of the invention in which an entrainment cell is used in conjunction with a mask.
Figure 14B:
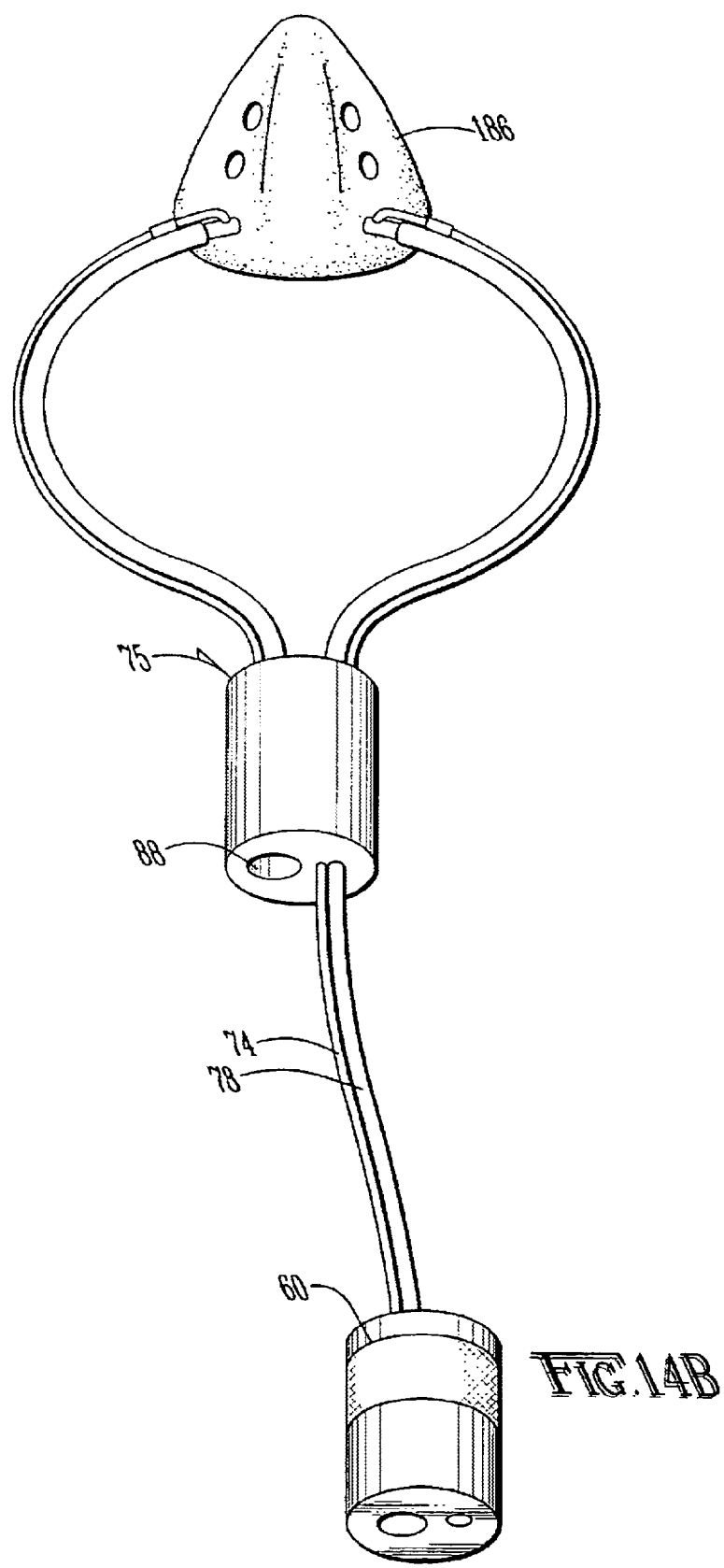
Figure 14C:
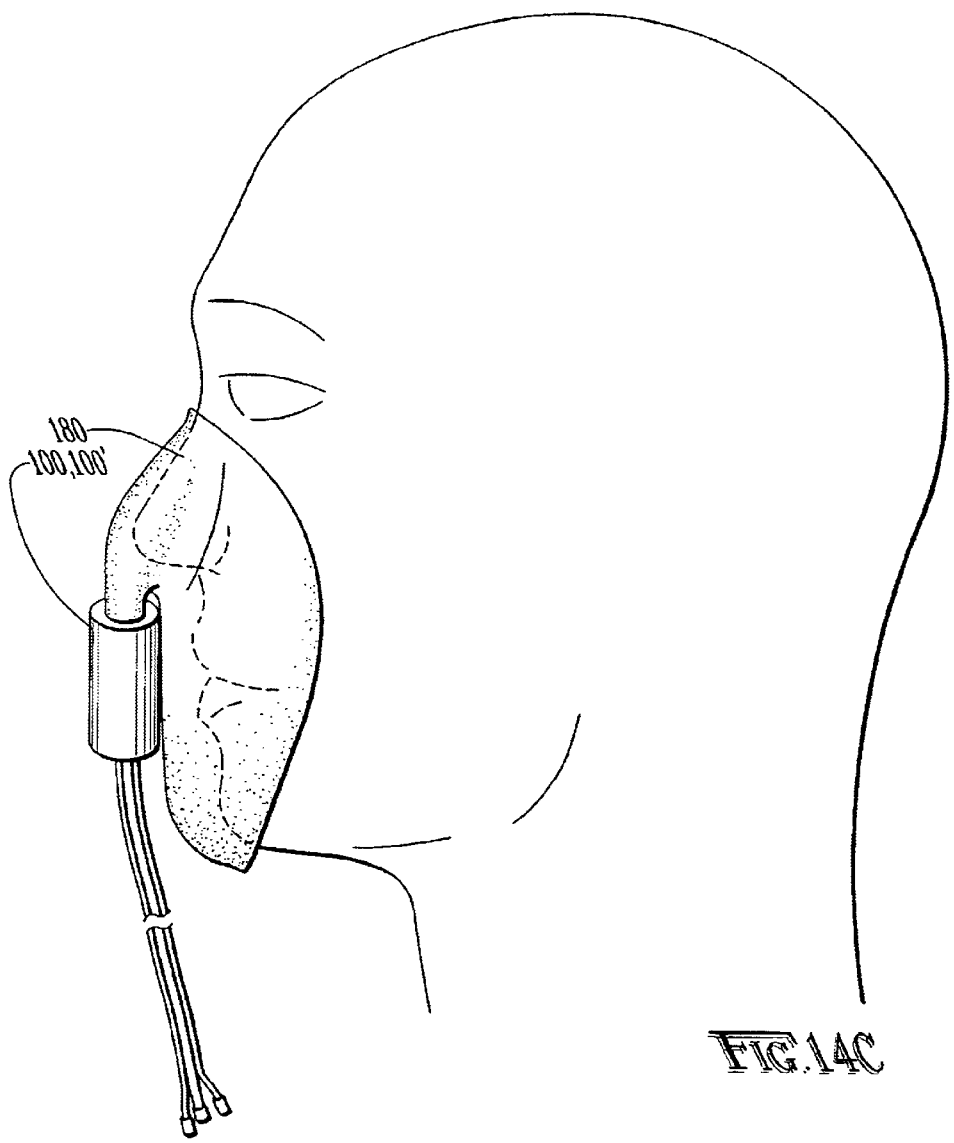
Figure 14D:
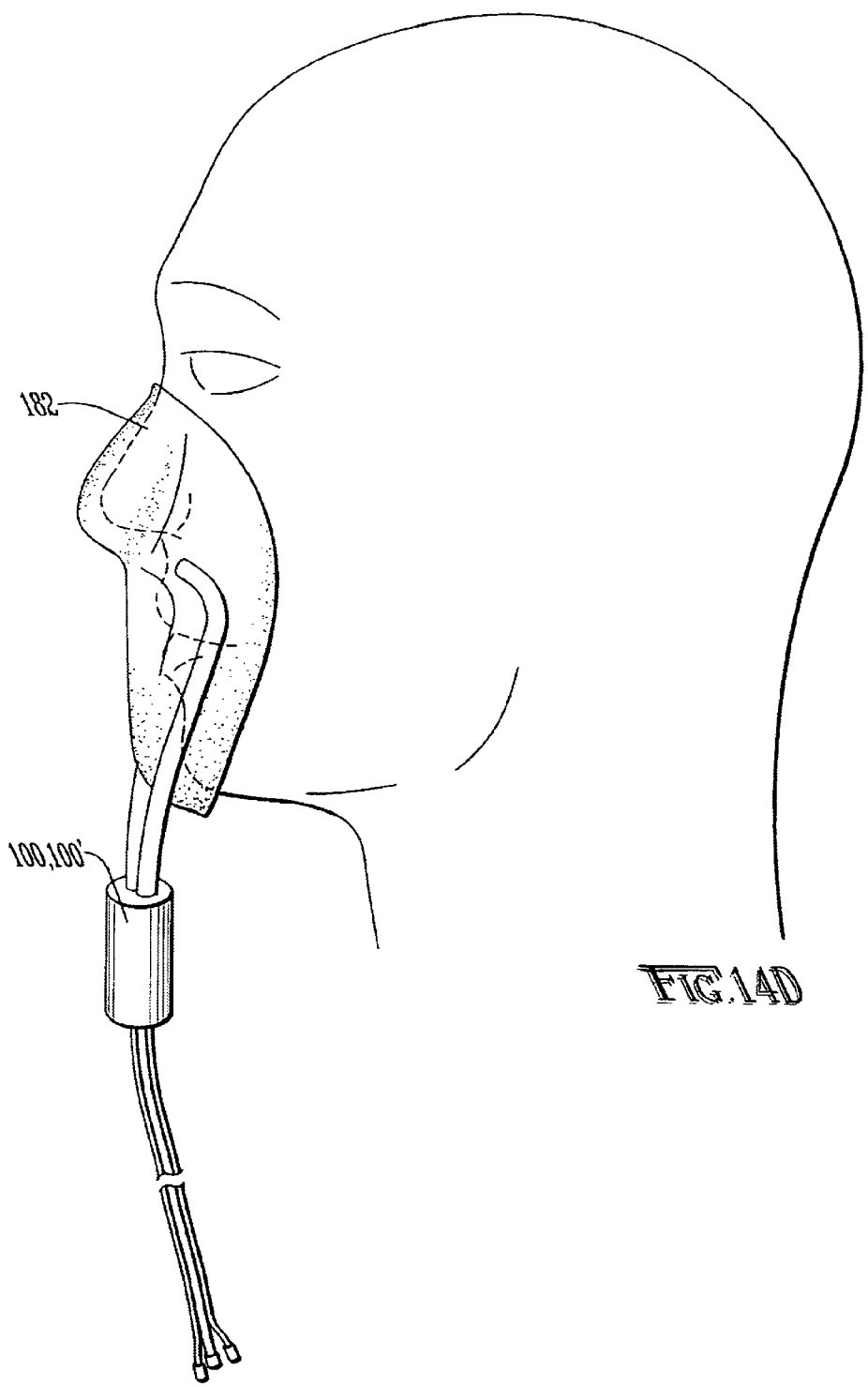

Yet further forms of the entrainment cell are shown in FIGS. 13A–13C. Entrainment cell 100$^V$ is shown in FIG. 13A as including a flow sensor 160 located in the interior volume of the cell. Flow sensor 160 is electrically connected to a sensor circuit (not shown) via electrical leads 162 which are located in a conduit 164 that extends through inlet end wall 104$^V$. Conduit 164 may also carry a therapeutic gas. The flow sensor is shown in FIG. 13A as being used in connection with a baffle, but could be used without the baffle if suitable. The flow sensor is located upstream of the air inlet port or ports and serves to verify that enough air is being entrained to sufficiently dilute the therapeutic gas or gases (if more than one therapeutic gas flows into the cell as by multiple therapeutic gas inlet lumens similar to lumen 120). The flow sensor can also be used to detect breath. When inspiration begins, air will flow through the cell and the flow sensor may be used to sense the beginning of inspiration. A pulse of therapeutic gas (or gases) that are coordinated with inspiration could then be triggered. The breath could be potentially detected sooner if the breath detecting sensor is located in the cell rather than in the instrument that the cannula is connected to (gas controller). This is because the delay in the pressure/flow signal propagation from the cell to the gas controller is avoided or bypassed in this embodiment. The flow sensor can also be used to measure the respiratory flow if the fraction of respiratory flow that travels through the device is a known relation of total flow. If respiratory flow is measured then the therapeutic gas delivery can be adjusted to respond to changes in respiratory flow. When a check valve 150 is included over the air entrainment port, the flow sensor can register approximately zero during exhalation even if the flow sensor is not flow direction sensitive. The check valve 150 provides half wave rectification of the flow signal.

It is also noted that there may be more than one outlet lumen associated with the entrainment cell. The outlet lumen, or lumens, has the following characteristics: tubing width: the tubing is large enough to cause only a small flow restriction at the applicable flow rates of gas through the tubing; tubing volume: the tubing volume is small enough so the transit time of gas is acceptably small; unrestrictive connections and geometry: the geometry of the tubing connectors and the flow path are designed to cause only a small flow restriction at the applicable flow rates of gas through the cannula; transparent: the tubing is in some forms of the invention transparent for easy inspection for debris and the like; detachable: the tubing is easily detached from the entrainment cell for easy exchange or cleaning.

The gas inlet lumen also extends parallel to the long axis of the entrainment cell (i.e., direction of dimension L in FIG. 9) to keep the cell oriented parallel to the patient's chest in normal operation.

As shown in FIG. 13B, flow check valves 320 may be included to reduce diffusion of gases back into the therapeutic gas lumens from beyond the lumens when the therapeutic gas flow is off. This may reduce pollution of the therapeutic gas.

In some cases, a therapeutic gas is to be mixed with the gases from the entrainment cell near the patient's nose. Such a form is shown as entrainment cell 100$^{VI}$ in FIG. 13C. A lumen 168 extends through cell 100$^{VI}$ parallel to the cell longitudinal axis from inlet end wall 102$^{VI}$ to and through outlet end wall 108$^{VI}$ to extend along the branches of lumen 124$^{VI}$ as shown in FIG. 13C.

Cell 100$^{VI}$ establishes a mixing region near the patient. Since gas is not injected into the entrainment cell, the low pass filter effect of the small entrainment cell can be avoided for the gas administered using lumen 168. Use of lumen 168 also reduces transit time of the gas from the mixing point to the patient and increases the pressure drop at the tip of lumen 168 over that of the pressure drop inside the cell. This pressure drop can be transmitted back through the lumen and makes the beginning of inspiration easier to detect. This is especially helpful if pulsed administration is used. Furthermore, flow of gas from lumen 168 does not influence the measurement of the entrained air flow and there is less delay between gas injection and delivery to the patient than if the gas is injected in the cell. The time for gases to react is also reduced using the form of the cell shown in FIG. 13C.

Referring again to FIG. 5, it is noted that the cannula 70 includes nasal prongs 92. These prongs are fluidically connected to the interior of the entrainment cell and fit into the patient's nares. The prongs are sized to be wide enough that a large fraction of the inspired gases will be drawn through the cannula yet small enough so the patient can exhale even when no exhaled air is permitted to flow into the cannula. The nasal prongs not only administer diluted therapeutic gas or gases to the patient, they also transmit the negative pressure (negative with respect to atmosphere) that occurs at the patient's nares during inspiration to the device so that air will be entrained and inspiration can be sensed. In the preferred form, the nasal prongs have an inside diameter of approximately 0.5 cm and an outside diameter of approximately 0.64 cm.

As discussed above, the entrainment cell disclosed herein can be used in connection with either a cannula or a mask. The cannula has been discussed above. Referring to FIGS. 14A–14D, masks 180 and 182 are shown in association with an entrainment cell. Mask 180 in FIG. 14C has an entrainment cell located immediately adjacent to a nose portion of the mask; whereas, mask 182 in FIG. 14D has the entrainment cell spaced from the nose portion of the mask. Mask 184 in FIG. 14A has two therapeutic gases which are mixed in the entrainment cell or near an upstream end of the entrainment cell; whereas mask 186 shown in FIG. 14B has two therapeutic gases with one being mixed immediately adjacent to the patient's nose.

Use of a mask in conjunction with an entrainment cell seals the patient's face so that all of the inspired respiratory gas flows through the entrainment cell.

Alternative forms of the mask have check valves on the mask to permit patient exhalation but will occlude room air from flowing into the mask and other forms can have multiple air ports. The air ports, like the above-discussed air ports can have any suitable shape.

Further embodiments of the system are shown in FIGS. 19 and 20. The entrainment cell can be located at any convenient position including spaced from the patient, or, as shown in FIG. 19, with entrainment cell EC located behind the patient's ear. Other convenient locations for the entrainment cell will occur to those skilled in the art based on the teaching of the present disclosure, and those locations are intended to be included within the scope of the present disclosure as well. As shown in FIG. 19, an inlet cannula. ECI fluidically connects entrainment cell EC and a flow sensor FSEC is located inside entrainment cell, with a lumen ECO fluidically connecting entrainment cell EC to the patient. The other forms of the entrainment cell, such as a cell including baffles or ports or the like as discussed herein can be used with entrainment cell EC as well.

Yet another form of the invention is shown in FIG. 20, in which a entrainment cell EB includes a shaped orifice So therewithin. A flow sensor EBS is also included in cell EB. Cell EB can be used in any of the embodiments disclosed herein as well.

Pressure Equalization Valve

Figure 15:
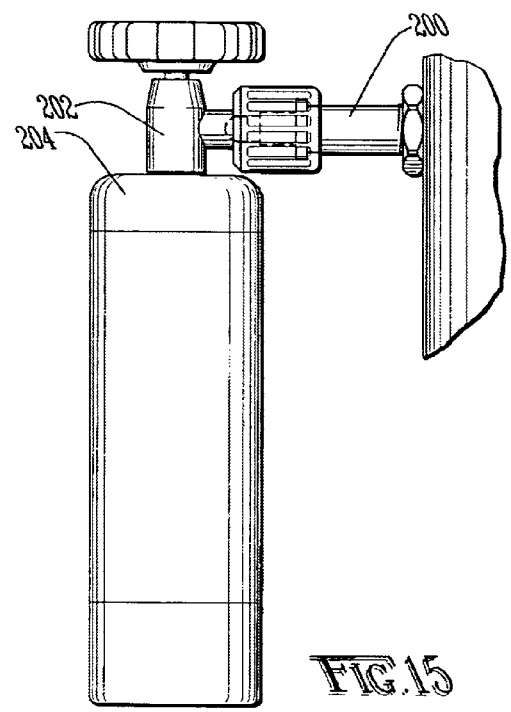
FIG. 15 is a pressure equalization valve in conjunction with a source of gas as used in conjunction with a system embodying the present invention.
Figure 16:
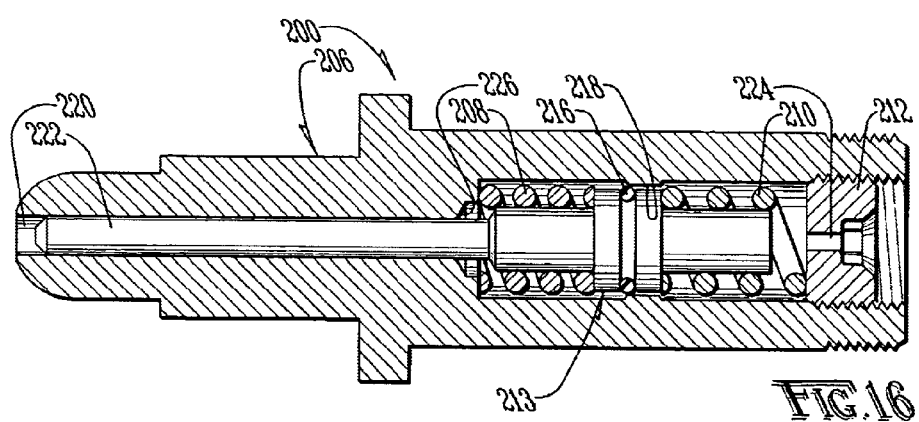
FIG. 16 shows the pressure equalization valve of FIG. 15 in a first condition.
Figure 17:
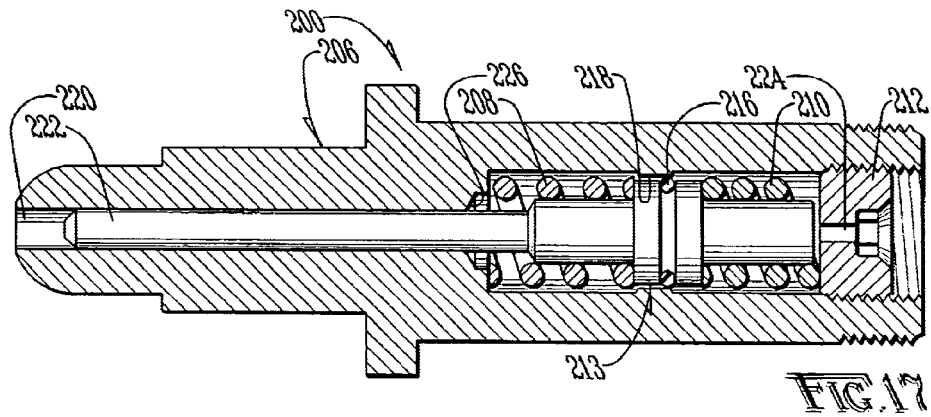
FIG. 17 shows the pressure equalization valve of FIG. 15 in another condition.
Figure 18A:
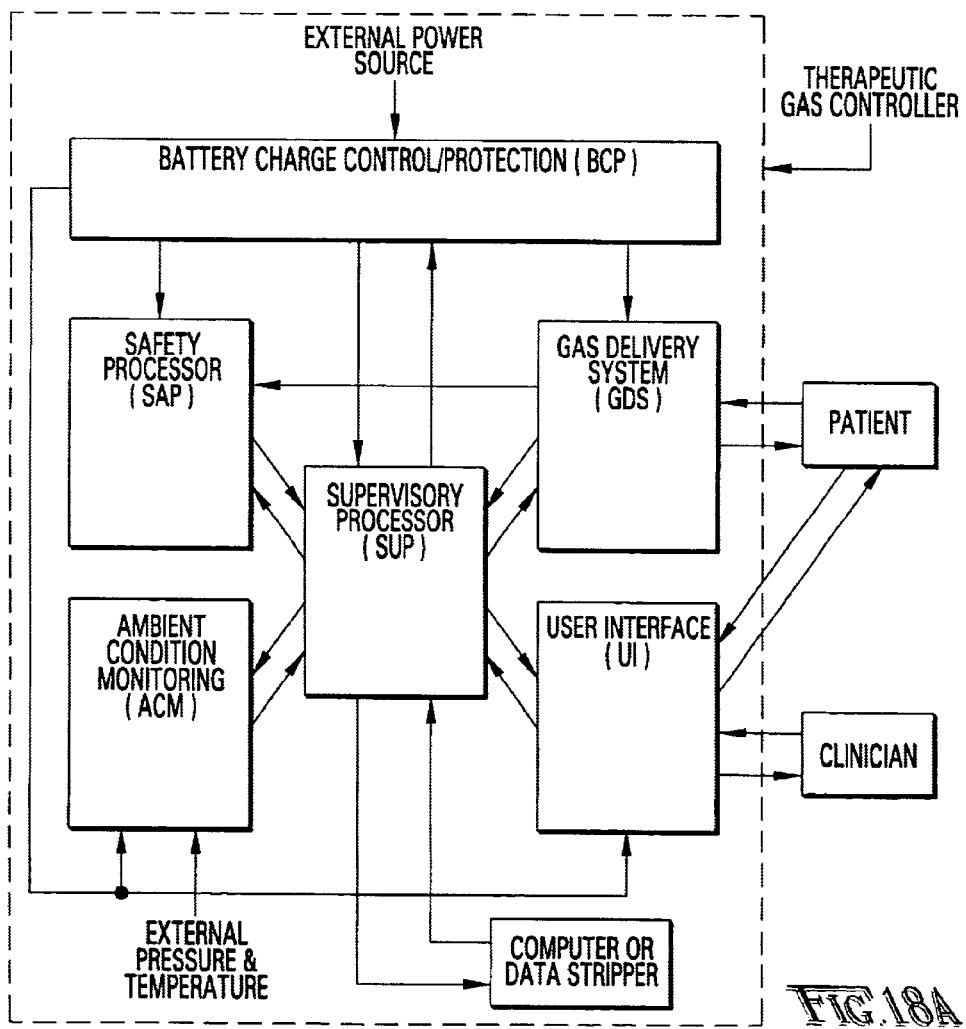
FIGS. 18A–18F show block diagrams of supervisory and control elements used in the system embodying the present invention.
Figure 18B:
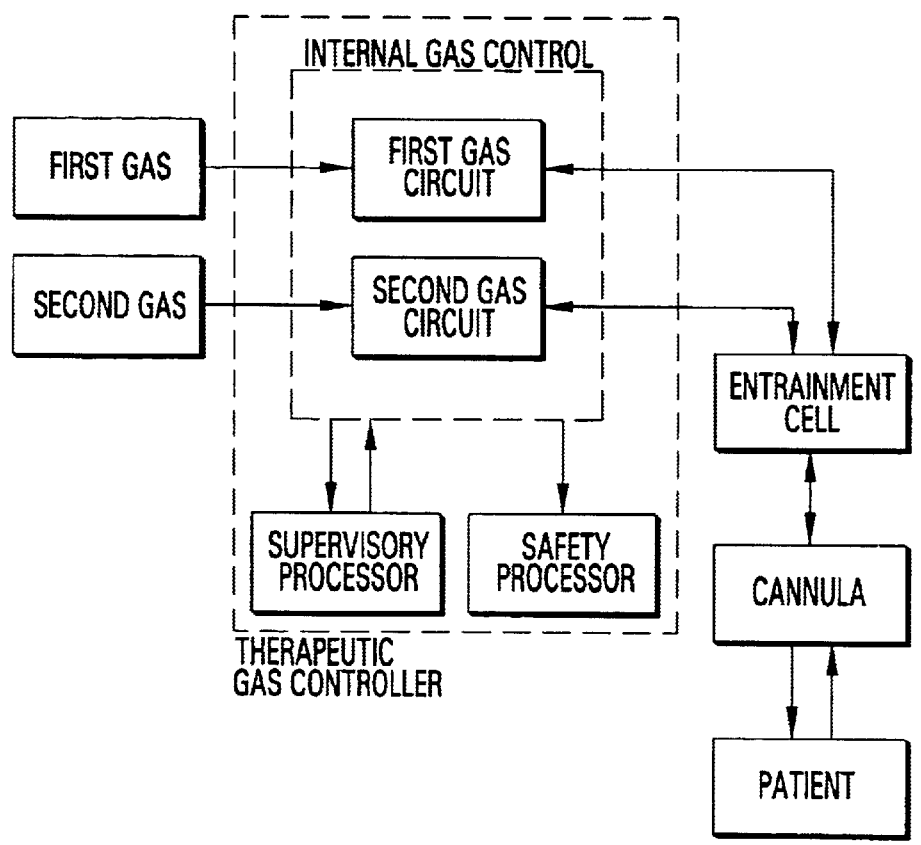
Figure 18C:
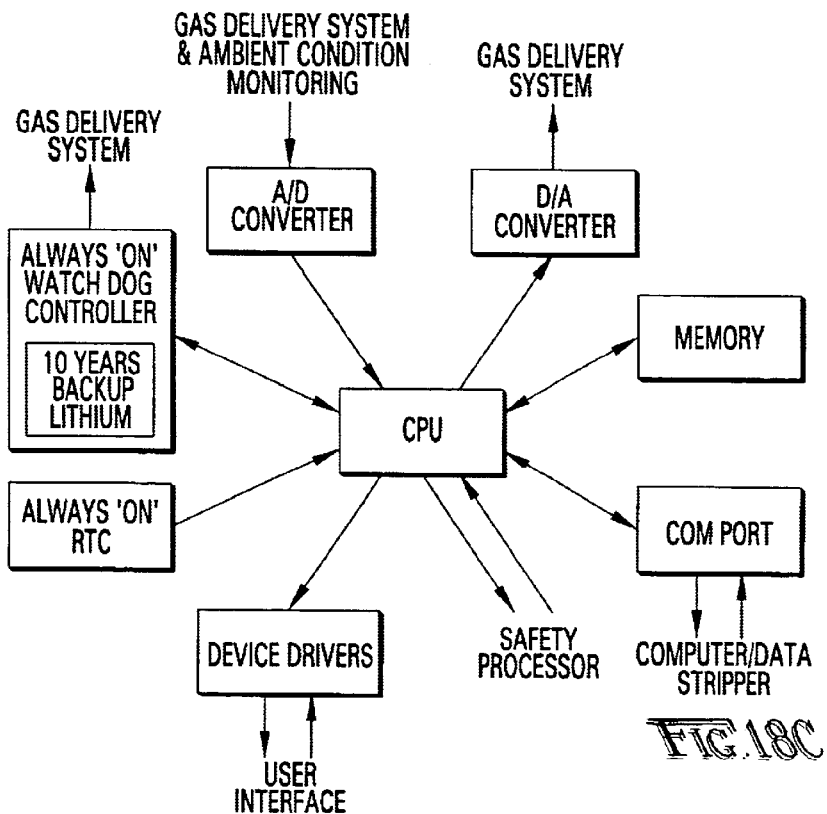
Figure 18D:
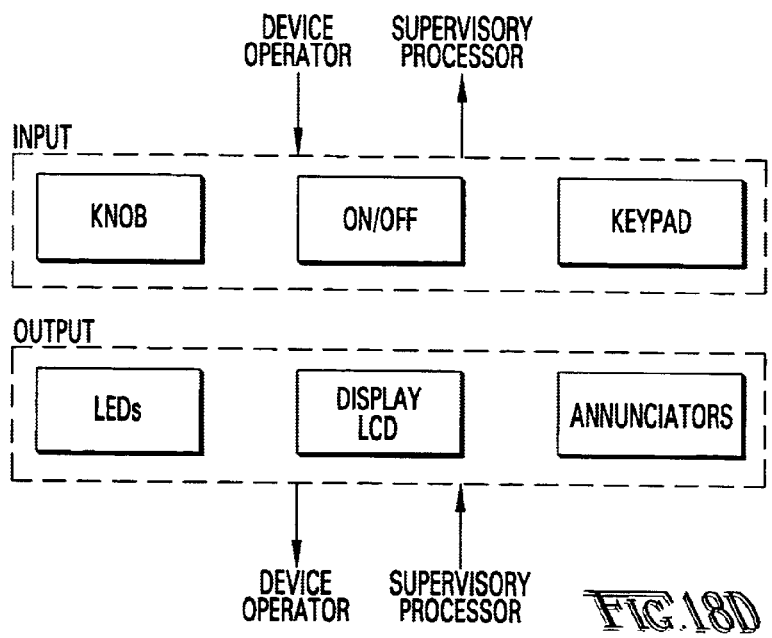
Figure 18E:
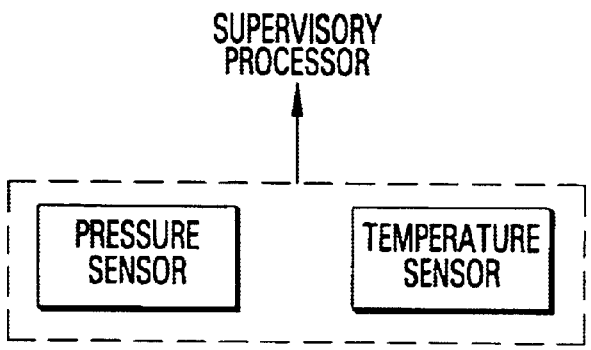
Figure 18F:
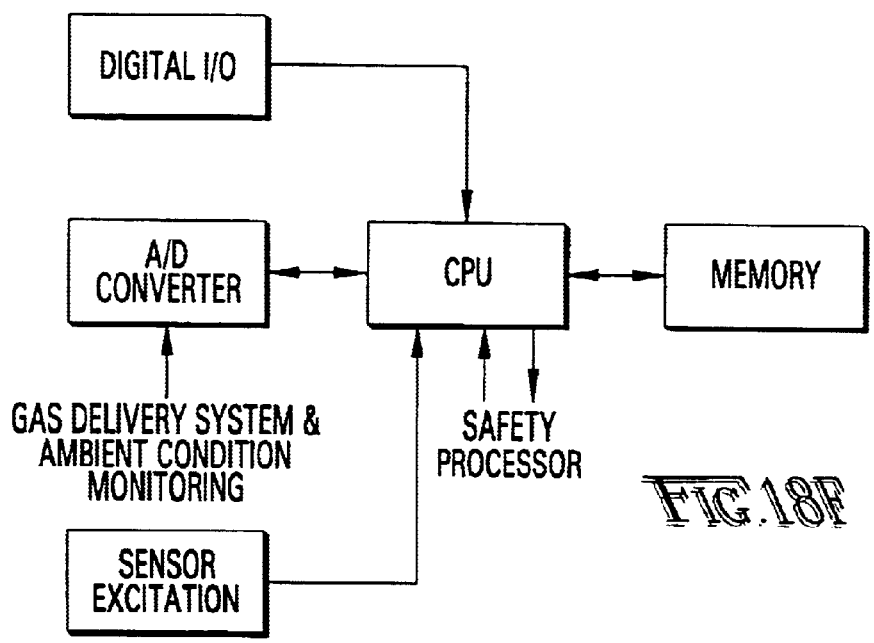

Referring next to FIGS. 15, 16 and 17 a pressure equalization valve 200 is shown that equalizes pressure on the two sides of the valve until the pressure on the high side of the valve is less than or equal to the pressure on the low side plus the difference that will be referred to as the equalization pressure.

The valve may have a symmetrical pressure flow characteristic where the equalization pressure is the same regardless of which side of the valve is high, or it may have an asymmetrical characteristic with a different equalization pressure depending on which side of the valve has the higher pressure. That is: (high side pressure—low side pressure) ≦equalization pressure 1, cylinder pressure is higher than system pressure (high side pressure—low side pressure) ≦equalization pressure 2, system pressure is higher than cylinder pressure equalization pressure 1=equalization pressure 2 in the symmetrical case.

Valve 200 is useful as a valve at the inlet of a gas system where a pressurized cylinder is connected as shown in FIG. 15. The equalization valve is connected directly to cylinder valve 202 of cylinder 204.

This valve keeps the system positively pressurized when a cylinder is removed while allowing the system to detect when a cylinder is disconnected and reconnected by monitoring the pressure at pressure sensor 18 (see FIG. 1). A normal pressure check valve with the cylinder on the inlet side of the valve would keep the system pressurized when a cylinder is disconnected but would not allow the detection of a cylinder change in all situations. Consider the case where the system is not delivering gas or purging. The pressure on the system side of the check valve would not change when the cylinder was disconnected and then a cylinder of the same or lower pressure was reconnected and the cylinder valve opened. The system could not detect a cylinder change in this scenario.

With the pressure equalization valve, the pressure on the system side of the valve drops to atmospheric pressure plus equalization pressure 2 when a cylinder is removed. The system remains pressurized to greater than atmospheric pressure. When a sufficiently pressurized cylinder is reconnected and the cylinder valve opened, the system pressure rises to the cylinder pressure minus equalization pressure 1. As long as the cylinder pressure is greater than equalization pressure 1+equalization pressure 2, the system can detect the cylinder change.

As shown in FIG. 16, valve 200 includes a plunger 213 housed inside a valve body 206. Two springs 208 and 210 are located on either side of the plunger. A vented set screw 212 is located on the system side of the valve and retains the plunger and the springs in the valve. The springs are chosen such that the plunger is positioned so that O-ring 216 is positioned somewhere on sealing surface 218 inside the valve body when the spring forces are equal. The springs may be chosen to give the desired equalization pressures. If the pressure on the system side of the valve is greater than the pressure on the cylinder side by more than equalization pressure 2, the plunger will be pushed toward the cylinder side until the O-ring clears the sealing surface. This is the situation that will occur if the system side of the valve is pressurized to greater than equalization pressure 2 and the cylinder is removed. Gas will then pass through the valve from the system side to the cylinder side.

Valve channel 220 is larger than valve pin 222 so that gas can flow through the channel. The flow rate through the valve is limited by the size of orifice 224. If the flow rate is high, the plunger will seat against plunger stop 226 and flow will be checked. Gas will flow until the pressure on the system side is equal to the pressure on the cylinder side plus equalization pressure 2. At this point, the O-ring will seat on the sealing surface and gas will cease flowing. The plunger will be positioned as shown in FIG. 16. The plunger pin 222 fills valve channel 220 so that debris does not enter the valve from this side. If gas is not flowing on the system side of the valve, then the system side of the valve will remain pressurized at equalization pressure 2.

When pressure on the cylinder side of the valve is raised to greater than the pressure on the system side plus equalization pressure 1, then the plunger will be pushed toward the system side until the O-ring clears the sealing surface. This will happen when a new pressurized cylinder is connected. Gas will then flow through the valve until the pressure on the system side equals the pressure on the cylinder side minus equalization pressure 1. At very high flow rates, the plunger will seat against the set screw and flow will be checked. Once the pressure on the system side equals the pressure on the cylinder side minus equalization pressure 1, the O-ring will seat against the sealing surface. The plunger will be positioned as shown in FIG. 17.

Several key features of valve 200 are as follows. |cylinder side pressure-system side pressure|≦equalization pressure. Where the equalization pressure may depend on which side of the valve is at higher pressure.

The system side is kept pressurized when a cylinder is removed as long as gas does not flow from the system side (away from the valve). This helps preserve the cleanliness of the system side circuit.

The pin fills the cylinder side of the valve when the cylinder is removed. This has two advantages: this reduces the possibility of debris entering the valve; and reduces the dead lo space where contaminating gas can be trapped during cylinder changing.

The orifice limits the flow rate through the valve.

The valve operates as a simple check valve for flow in both directions.

Several variations of valve 200 are possible within the scope of the teaching of the present disclosure. As already mentioned, the equalization pressure may or may not be different when the pressure is greater on the system side than it is when the pressure on the cylinder side is greater. This can be accomplished in several ways. For example, the spring constants of the two springs can be varied. Alternatively, the position of the sealing surface can be moved. Those skilled in the art will understand other variations based on the teaching of this disclosure and such variations are intended to be included in this disclosure.

Figure 21:
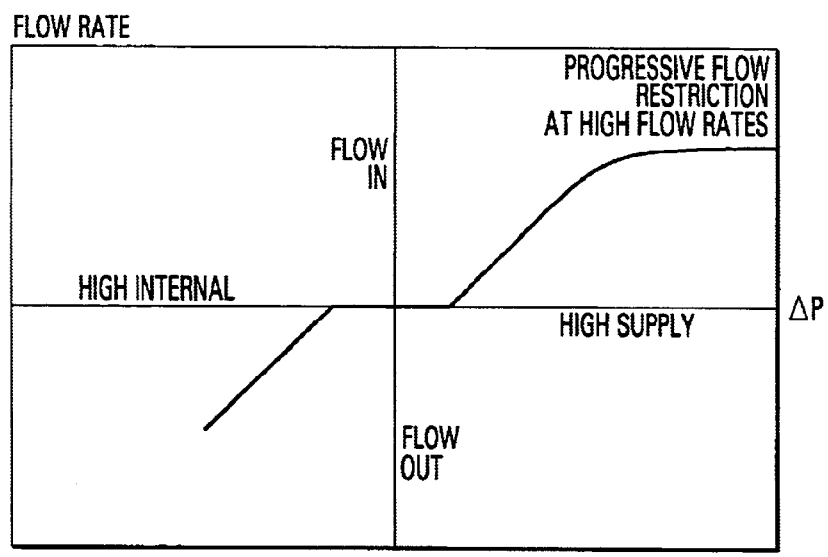
FIG. 21 shows flow rate versus $\Delta P$ for the equalizing valve of the present invention.

Referring to FIG. 21, it can be understood that by providing a flow versus pressure dead band situated around zero differential pressure across the equalizing valve, the valve of the present invention mutually meets the requirements for maintaining a sealed system and allowing a supply connection or disconnection to be detected.

It can be understood from the foregoing disclosure that the equalizing valve of the present invention provides a low dead volume pressure equalizing device that provides a flow versus pressure dead band that provides for zero flow in either direction at non-zero differential pressures. The dead band may be symmetric or asymmetric in differential pressure about zero with respect to a non-zero flow in either direction through the valve. As can be seen in the figures, the pin is sized to minimize the dead space and the springs have their spring characteristics, including the length as well as the force versus displacement characteristics of the springs so the plunger is located in an intermediate region of plunger travel when flow is prohibited and so the dead band is either symmetric or asymmetric in differential pressure about zero with respect to non-zero flow in each direction. As can also be understood from the foregoing disclosure, the valve can incorporate a progressive flow restriction safety mechanism that prevents high flow rates in the event of an otherwise unconstrained flow.

It is understood that while certain forms of the present invention have been illustrated and described, it is not limited to the specific forms or parts arrangements described and shown.

What is claimed is:

1. A device for use in administering therapeutic gas to a spontaneously breathing, non-ventilated patient comprising:
    A) a hollow entrainment cell having an inlet location and an outlet location with an outlet port fluidically connected to the interior of said entrainment cell for conducting therapeutic gas to a patient for administering therapeutic gas to the patient and a gas inlet port fluidically connected to a source of therapeutic gas, an air inlet port defined through a wall of said entrainment cell and fluidically connecting the interior of said entrainment cell with ambient air;
    B) said entrainment cell being located remotely from a patient's nares to which gas from said entrainment cell is to be conducted for administration to the patient; and
    C) said entrainment cell being sized to provide a low temporal latency for gases flowing through said entrainment cell.

2. The device defined in claim 1 wherein said temporal latency is less than 100 milliseconds.

3. The device defined in claim 1 wherein said entrainment cell is cylindrical with an inlet location wall and an outlet location wall and a side wall connecting said inlet location wall to said outlet location wall.

4. The device defined in claim 3 further including a check valve on said air inlet port and oriented to permit air flow into said entrainment cell and to occlude said air inlet port against gas flow out of said entrainment cell.

5. The device defined in claim 3 wherein said air inlet port is located in said inlet location wall.

6. The device defined in claim 5 further including an inlet lumen connected to said inlet port and is located in said inlet location wall adjacent to said air inlet port.

7. The device defined in claim 6 further including a shaped orifice inside said entrainment cell.

8. The device defined in claim 6 further including a flow baffle positioned internally of said entrainment cell between said inlet location wall and said outlet location wall.

9. The device defined in claim 8 wherein said baffle includes a single hole through which gases pass.

10. The device defined in claim 8 wherein said baffle includes a multiplicity of holes through which gases pass.

11. The device defined in claim 8 further including an inlet lumen fluidically connected to the inlet port of said entrainment cell and an inlet lumen extension extending from said inlet location wall past said baffle.

12. The device defined in claim 1 further including a second air inlet port defined through the side wall of said entrainment cell.

13. The device defined in claim 1 further including a flow rate sensor located in said entrainment cell.

14. The device defined in claim 1 further including a gas conduit fluidically connecting a second source of therapeutic gas to said entrainment cell.

15. The device defined in claim 1 further including a connector for connecting the device to a gas controller, said connector having means to identify to the controller the type and characteristics of the device.

16. The device defined in claim 1 wherein said entrainment cell is located remote from the patient.

17. The device defined in claim 1 wherein the total amount of gases in said entrainment cell plus the total amount of gases in the conduits fluidically connecting said entrainment cell to the patient is less than 50% of the volume of the patient's inspiratory flow during a single breath.

18. The device defined in claim 1 wherein the volume of the patient's inspiratory flow during a single breath is between 5 ml and 500 ml.

19. The device defined in claim 1 wherein the the total amount of gases in the entrainment cell plus the total amount of gases in conduits fluidically connecting the entrainment cell to the patient is between 20% and 50% of the volume of the patient's inspiratory flow during a single breath.

20. A device for use in administering therapeutic gas to a spontaneously breathing, non-ventilated patient comprising:
    A) a hollow entrainment cell having an inlet location and an outlet location with an outlet port fluidically connected to the interior of said entrainment cell for conducting therapeutic gas to a patient for administering therapeutic gas to the patient, and an air inlet port defined through a wall of said entrainment cell and fluidically connecting the interior of said entrainment cell with ambient air;
    B) said entrainment cell being located remotely from a patient's nares;
    C) said entrainment cell being sized to provide a low temporal latency for gases flowing through said entrainment cell;
    D) a lumen fluidically connected to the patient's nares and conducting therapeutic gas past said entrainment cell to a location near the patient where therapeutic gas is mixed with entrained air prior to delivery to the patient whereby cannula latency is reduced.

21. The device defined in claim 1 further including a mask which is positioned on the patient for delivering therapeutic gas to the patient, and fluid connections fluidically connecting said mask with the outlet location of said entrainment cell.

22. The device defined in claim 21 wherein the fluid connections fluidically connecting the mask to the outlet location of the entrainment cell include a lumen.

23. The device defined in claim 1 wherein said entrainment cell has an internal volume of less than 10 $cm^3$.

24. The device defined in claim 23 wherein said entrainment cell has a length dimension and a diameter dimension with the length dimension being greater the diameter dimension.

25. The device defined in claim 24 wherein the length dimension of said entrainment cell is greater than three times the diameter dimension of said entrainment cell.

26. The device defined in claim 1 further including a flow detector fluidically connected to the patient for detecting inspiration.

27. The device defined in claim 1 further including an interlocking connector that interlocks the device to a gas controller, said interlocking connector including means to indicate to said controller when said interlocking connector is not properly engaged.

28. The device defined in claim 1 further including an outlet gas port fluidically connected to an outlet lumen.

29. The device defined in claim 28 further including a plurality of outlet lumens.

30. The device defined in claim 28 wherein said outlet gas port has a flow dimension smaller than a flow dimension of the outlet lumen.

31. The device defined in claim 1 further including a therapeutic gas controller for controlling delivery of therapeutic gas to the patient according to patient inspiration.

32. The device defined in claim 31 wherein said therapeutic gas controller includes a pressure sensor located to sense beginning of patient inspiration.

33. The device defined in claim 1 wherein a total volume of gases are conducted into said entrainment cell via said gas inlet port and said air inlet port, said air inlet port and said gas outlet port being sized so the total volume of gases is greater than twenty percent of the total patient inspiratory flow on a breathing cycle.

34. The device defined in claim 20 further including a gas inlet port fluidically connected to a source of therapeutic gas.

35. The device defined in claim 20 wherein the volume of the patient's inspiratory flow during a single breath is between 5 ml and 500 ml.

36. The device defined in claim 20 wherein the the total amount of gases in the entrainment cell plus the total amount of gases in conduits fluidically connecting the entrainment cell to the patient is between 20% and 50% of the volume of the patient's inspiratory flow during a single breath.

37. A device for use in administering therapeutic gas to a spontaneously breathing patient comprising:

A) a non-ventilated patient;

B) a hollow entrainment cell having an inlet location and an outlet location with an outlet port fluidically connected to the interior of said entrainment cell for conducting therapeutic gas to said patient for administering therapeutic gas to said patient and a gas inlet port fluidically connected to a source of therapeutic gas, an air inlet port defined through a wall of said entrainment cell and fluidically connecting the interior of said entrainment cell with ambient air;

C) said entrainment cell being located remotely from said patient's nares to which gas from said entrainment cell is to be conducted for administration to the patient; and D) said entrainment cell being sized so a total amount of gases in said entrainment cell plus a total amount of gases in conduits fluidically connecting said entrainment cell to the patient at any time during said patient's breathing cycle is less than a volume of said patient's inspiratory flow during the breathing cycle to provide a low temporal latency for gases flowing through said entrainment cell.

38. The device defined in claim 37 wherein the volume of the patient's inspiratory flow during the breathing cycle is between 5 ml and 500 ml.

39. A device for use in administering therapeutic gas to a spontaneously breathing, non-ventilated patient comprising:

A) a hollow entrainment cell having an inlet location and an outlet location with an outlet port fluidically connected to the interior of said entrainment cell for conducting therapeutic gas to a patient for administering therapeutic gas to the patient and a gas inlet port fluidically connected to a source of therapeutic gas, an air inlet port defined through a wall of said entrainment cell and fluidically connecting the interior of said entrainment cell with ambient air;

B) said entrainment cell being located remotely from a patient's nares to which gas from said entrainment cell is to be conducted for administration to the patient; and C) said entrainment cell being sized so a total flow rate of gases in the device during inspiration of the patient, including entrained air, is a fraction of the patient's inspiratory flow rate.

40. The device defined in claim 39 wherein the fraction of the patient's inspiratory flow rate is between 20% and 50%.

41. A device for use in administering therapeutic gas to a spontaneously breathing, non-ventilated patient comprising:

A) a hollow entrainment cell having an inlet location and an outlet location with an outlet port fluidically connected to the interior of said entrainment cell for conducting therapeutic gas to a patient for administering therapeutic gas to the patient and a gas inlet port fluidically connected to a source of therapeutic gas, an air inlet port defined through a wall of said entrainment cell and fluidically connecting the interior of said entrainment cell with ambient air;

B) said entrainment cell being located remotely from a patient's nares to which gas from said entrainment cell is to be conducted for administration to the patient; and C) said entrainment cell being sized to provide a temporal latency for gases flowing through said entrainment cell of less than 100 milliseconds.

* * * * *